US008905950B2

(12) United States Patent
Bonutti et al.

(10) Patent No.: US 8,905,950 B2
(45) Date of Patent: Dec. 9, 2014

(54) SHOULDER ROM ORTHOSIS

(75) Inventors: Peter M. Bonutti, Effingham, IL (US); Boris P. Bonutti, Effingham, IL (US); Kevin R. Ruholl, Effingham, IL (US); Glen A. Phillips, Effingham, IL (US)

(73) Assignee: Bonutti Research, Inc., Effingham, IL (US)

( * ) Notice: Subject to any disclaimer, the term of this patent is extended or adjusted under 35 U.S.C. 154(b) by 1125 days.

(21) Appl. No.: 12/392,012

(22) Filed: Feb. 24, 2009

(65) Prior Publication Data

US 2009/0264799 A1 Oct. 22, 2009

Related U.S. Application Data

(60) Provisional application No. 61/033,716, filed on Mar. 4, 2008.

(51) Int. Cl.
*A61H 1/02* (2006.01)
*A61F 5/04* (2006.01)

(52) U.S. Cl.
CPC ...... *A61H 1/0237* (2013.01); *A61H 2201/5064* (2013.01); *A61H 2201/5082* (2013.01); *A61H 1/0274* (2013.01)
USPC ................. 601/33; 601/5; 128/878; 128/845; 602/16; 602/36

(58) Field of Classification Search
CPC . A61H 1/0274; A61H 1/0277; A61H 1/0281; A61H 2201/1614; A61H 2201/1616; A61H 2201/1635; A61H 2201/1638
USPC ................ 602/16, 35–36; 128/878–879, 862, 128/845–846; 16/366, 239; 242/385, 396.2, 242/396.4; 601/33, 5
See application file for complete search history.

(56) References Cited

U.S. PATENT DOCUMENTS

| | | | |
|---|---|---|---|
| 432,327 | A | 7/1890 | Page |
| 433,227 | A | 7/1890 | Beacock |

(Continued)

FOREIGN PATENT DOCUMENTS

| | | |
|---|---|---|
| CA | 2066151 | 10/1992 |
| CA | 2065669 | 10/1993 |

(Continued)

OTHER PUBLICATIONS

Advertising materials from the Internet on Jun. 5, 1998 entitled: “Quadrant by Smith & Nephew DonJoy”. “Entering a New Plane”.
Advertising materials from the Internet on Jun. 5, 1998 entitled: “Make DonJoy’s Quadrant Your First Choice for Effective Post-Operative Shoulder Treatment”. “Quadrant Brace Specifications”.

(Continued)

*Primary Examiner* — Patricia Bianco
*Assistant Examiner* — Kari Petrik
(74) *Attorney, Agent, or Firm* — Armstrong Teasdale LLP

(57) ABSTRACT

Therapeutic abduction of the shoulder joint is achieved using a hinged device, the hinge activated by a cable passed between pulleys to increase mechanical advantage. The cable is wound on a spool mounted on a ratcheting mechanism, whereby tension is maintained as the spool is wound via a knob or computer controlled motor. A rotation control device enables rotation of the spool by a user, but prevents rotation due to a load. Mating shackles pivot in connection with the hinge, and are activated by the cable to increase the angle of the hinge. The hinge is connected to the body, one portion affixed relative to the body, the other affixed relative to the upper arm. As the hinge angle is expanded, the shoulder joint is abducted, stretching the tissue of the joint. If resilient, the cable imparts a dynamic tensioning force to the shoulder joint. Medial or lateral rotation is accomplished by a second device disposed at the elbow, wherein the pivot point of internal/external rotation is along the axis of the upper arm.

14 Claims, 25 Drawing Sheets

(56) References Cited

U.S. PATENT DOCUMENTS 2,191,283 A 2/1940 Longfellow
2,206,902 A 7/1940 Kost
2,223,276 A 11/1940 Ward
2,237,252 A 4/1941 Longfellow
2,246,689 A 6/1941 Kost
2,250,493 A 7/1941 Milne
2,590,729 A 3/1952 Scognamillo
2,590,739 A 3/1952 Wahner et al.
2,811,154 A 10/1957 Scholl
2,820,455 A 1/1958 Hall
2,829,562 A 4/1958 La Rue
2,832,334 A 4/1958 Whitelaw
3,083,708 A 4/1963 Gottfried
3,338,237 A 8/1967 Sconce
3,351,055 A 11/1967 Gottfried
3,548,818 A 12/1970 Kaplan
3,580,248 A 5/1971 Larson
3,698,389 A 10/1972 Guedel
3,701,349 A 10/1972 Larson
3,724,452 A 4/1973 Nitschke
3,760,056 A 9/1973 Rudy
3,795,243 A 3/1974 Miller
3,811,434 A 5/1974 Jacobson et al.
3,814,419 A 6/1974 Bjorklund et al.
3,856,004 A 12/1974 Cox
3,955,565 A 5/1976 Johnson, Jr.
3,970,316 A 7/1976 Westmoreland, Jr.
3,976,057 A 8/1976 Barclay
4,039,183 A 8/1977 Sakurada
4,076,022 A 2/1978 Walker
4,084,267 A 4/1978 Zadina
4,108,170 A 8/1978 Spann
4,180,870 A 1/1980 Radulovic et al.
4,214,577 A 7/1980 Hoy
4,229,001 A 10/1980 Roman
4,237,873 A 12/1980 Terry et al.
4,241,731 A 12/1980 Pauley
4,273,113 A 6/1981 Hofstein
4,285,773 A 8/1981 Taciuk
4,320,748 A 3/1982 Racette et al.
4,363,481 A 12/1982 Erickson
4,370,977 A 2/1983 Mauldin et al.
4,383,523 A 5/1983 Schurman
4,396,013 A 8/1983 Hasslinger
4,417,569 A 11/1983 Brudny
4,441,489 A 4/1984 Evans et al.
4,454,871 A 6/1984 Mann et al.
4,456,001 A 6/1984 Pescatore
4,456,002 A 6/1984 Barber et al.
4,502,470 A 3/1985 Kiser et al.
4,502,681 A 3/1985 Blomqvist
4,508,111 A 4/1985 Hepburn
4,509,509 A 4/1985 Bouvet et al.
4,538,595 A 9/1985 Hajianpour
4,538,600 A 9/1985 Hepburn
4,570,619 A 2/1986 Gamm
4,576,151 A 3/1986 Carmichael et al.
4,589,406 A 5/1986 Florek
4,606,542 A 8/1986 Segal
4,612,919 A 9/1986 Best
4,628,913 A 12/1986 Lerman
4,641,639 A 2/1987 Padilla
4,653,479 A 3/1987 Maurer
4,665,905 A 5/1987 Brown
4,693,239 A 9/1987 Clover, Jr.
4,716,889 A 1/1988 Saringer
4,718,665 A 1/1988 Airy et al.
4,727,865 A 3/1988 Hill-Byrne
4,739,334 A 4/1988 Soref
4,765,320 A 8/1988 Lindemann et al.
4,788,941 A 12/1988 Villeneuve
4,790,301 A 12/1988 Silfverskiold
4,793,334 A 12/1988 McGuinness et al.
4,805,601 A 2/1989 Eischen, Sr.
4,807,601 A 2/1989 Wright
4,809,688 A 3/1989 Aymerica del Valle et al.
4,834,073 A 5/1989 Bledsoe et al.
4,844,094 A 7/1989 Grim
4,844,454 A 7/1989 Rogers
4,844,455 A 7/1989 Funkhouser, Jr.
4,848,326 A 7/1989 Lonardo
4,862,877 A 9/1989 Barber
4,865,024 A 9/1989 Hensley et al.
4,869,267 A 9/1989 Grim et al.
4,869,499 A 9/1989 Schiraldo
4,884,454 A 12/1989 Johnson
4,913,135 A 4/1990 Mattingly
4,913,755 A 4/1990 Grim
4,930,497 A 6/1990 Saringer
4,953,543 A 9/1990 Grim et al.
4,955,369 A 9/1990 Bledsoe et al.
4,955,396 A 9/1990 Fralick et al.
4,957,281 A 9/1990 Christolear, Jr.
4,964,402 A 10/1990 Grim et al.
4,991,234 A 2/1991 Greenberg
4,996,979 A 3/1991 Grim et al.
5,005,563 A 4/1991 Veale
5,018,514 A 5/1991 Grood et al.
5,019,050 A 5/1991 Lynn et al.
5,025,782 A 6/1991 Salerno
5,027,688 A 7/1991 Suzuki et al.
5,027,801 A 7/1991 Grim
5,027,802 A 7/1991 Donohue
5,036,837 A 8/1991 Mitchell et al.
5,036,838 A 8/1991 Sherman
5,052,375 A 10/1991 Stark et al.
5,052,379 A 10/1991 Airy et al.
5,070,866 A 12/1991 Alexander et al.
5,078,128 A 1/1992 Grim et al.
5,088,481 A 2/1992 Darby
5,100,403 A 3/1992 Hotchkiss et al.
5,102,411 A 4/1992 Hotchkiss et al.
5,116,359 A 5/1992 Moore
5,125,400 A 6/1992 Johnson, Jr.
5,135,470 A 8/1992 Reeves
5,139,475 A 8/1992 Robicsek
5,141,489 A 8/1992 Sereboff
5,156,589 A 10/1992 Langen et al.
5,163,451 A 11/1992 Grellas
5,167,612 A 12/1992 Bonutti
5,191,903 A 3/1993 Donohue
5,197,942 A 3/1993 Brady
5,201,702 A 4/1993 Mars
5,201,772 A 4/1993 Maxwell
5,203,321 A 4/1993 Donovan et al.
5,203,766 A * 4/1993 Carter et al. .................... 602/21
5,211,161 A 5/1993 Stef
5,213,094 A 5/1993 Bonutti
5,213,095 A 5/1993 Dague
5,218,954 A 6/1993 van Bemmelen
5,226,245 A 7/1993 Lamont
5,232,435 A 8/1993 Leibinsohn
5,252,101 A 10/1993 Rosenwinkel et al.
5,252,102 A 10/1993 Singer et al.
5,261,125 A 11/1993 Cartwright et al.
5,277,695 A 1/1994 Johnson, Jr. et al.
5,285,773 A 2/1994 Bonutti et al.
5,297,540 A 3/1994 Kaiser et al.
5,312,322 A 5/1994 Santana
5,316,022 A 5/1994 Schiek, Sr.
5,323,435 A 6/1994 Baversten
RE34,661 E 7/1994 Grim
5,327,882 A 7/1994 Saringer et al.
5,328,448 A 7/1994 Gray, Sr.
5,329,705 A 7/1994 Grim et al.
5,348,530 A 9/1994 Grim et al.
5,349,956 A 9/1994 Bonutti
5,352,216 A 10/1994 Shiono et al.
5,354,260 A 10/1994 Cook
5,364,323 A 11/1994 Liu
5,365,947 A 11/1994 Bonutti
5,370,133 A 12/1994 Darby et al.
5,372,597 A 12/1994 Hotchkiss et al.
5,376,091 A 12/1994 Hotchkiss et al.

(56) References Cited

U.S. PATENT DOCUMENTS 5,378,223 A 1/1995 Grim et al.
5,385,536 A 1/1995 Burkhead et al.
5,389,065 A 2/1995 Johnson, Jr.
5,391,132 A 2/1995 Greenwald
5,395,303 A 3/1995 Bonutti et al.
5,399,152 A 3/1995 Habermeyer et al.
5,403,265 A 4/1995 Berguer et al.
5,407,420 A 4/1995 Bastyr et al.
5,407,422 A 4/1995 Matthijs et al.
5,417,643 A 5/1995 Taylor
5,419,757 A 5/1995 Daneshvar
5,421,874 A 6/1995 Pearce
5,435,009 A 7/1995 Schild et al.
5,437,611 A 8/1995 Stern
5,437,619 A 8/1995 Malewicz et al.
5,452,205 A 9/1995 Telepko
5,453,075 A 9/1995 Bonutti et al.
5,453,082 A 9/1995 Lamont
5,456,268 A 10/1995 Bonutti
5,456,286 A 10/1995 Warner et al.
5,464,385 A 11/1995 Grim
5,466,213 A 11/1995 Hogan et al.
5,466,250 A 11/1995 Johnson, Jr. et al.
5,472,407 A 12/1995 Schenck
5,472,410 A 12/1995 Hamersly
5,492,133 A 2/1996 McVicker
5,503,619 A 4/1996 Bonutti
5,503,622 A 4/1996 Wehr
5,503,908 A 4/1996 Faass
5,518,009 A 5/1996 Ruiz-Gonzalez
5,520,181 A 5/1996 Kreidler et al.
5,520,620 A 5/1996 Johnson
5,520,628 A 5/1996 Wehr
5,527,269 A 6/1996 Reithofer
5,531,669 A 7/1996 Varnau
5,535,274 A 7/1996 Braitberg et al.
5,538,486 A 7/1996 France et al.
5,571,077 A 11/1996 Klearman et al.
5,575,764 A 11/1996 Van Dyne
5,577,998 A 11/1996 Johnson, Jr. et al.
5,605,535 A 2/1997 Lepage
5,609,570 A 3/1997 Lamont
5,611,764 A 3/1997 Bonutti et al.
5,620,411 A 4/1997 Schumann et al.
5,626,537 A 5/1997 Danyo et al.
5,647,378 A 7/1997 Farnum
5,653,680 A 8/1997 Cruz
5,665,059 A 9/1997 Klearman et al.
5,681,269 A 10/1997 Basaj et al.
5,685,830 A 11/1997 Bonutti
5,749,840 A 5/1998 Mitchell et al.
5,755,679 A 5/1998 Selner et al.
5,761,834 A 6/1998 Grim et al.
5,772,619 A 6/1998 Corbett
5,778,565 A 7/1998 Holt et al.
5,788,659 A 8/1998 Haas
5,792,084 A 8/1998 Wilson et al.
5,820,577 A 10/1998 Taylor
5,823,975 A 10/1998 Stark et al.
5,833,639 A 11/1998 Nunes et al.
5,839,139 A 11/1998 Fink
5,848,979 A 12/1998 Bonutti et al.
5,865,773 A 2/1999 Koledin
5,882,320 A 3/1999 Peterson
5,882,323 A 3/1999 Belkin
5,919,148 A 7/1999 Marko et al.
5,929,782 A 7/1999 Stark et al.
5,940,992 A 8/1999 Darby
5,943,705 A 8/1999 Sink
5,951,499 A 9/1999 Saringer et al.
5,980,435 A 11/1999 Joutras et al.
6,001,075 A 12/1999 Clemens et al.
6,007,500 A 12/1999 Quintinskie, Jr.
6,015,110 A * 1/2000 Lai ............................ 242/388.1
6,021,780 A 2/2000 Darby
6,027,468 A 2/2000 Pick
6,053,169 A 4/2000 Hunt
6,059,576 A 5/2000 Brann
6,076,266 A 6/2000 Beckingham et al.
6,093,162 A 7/2000 Fairleigh et al.
6,099,489 A 8/2000 Herzberg et al.
6,113,562 A 9/2000 Bonutti et al.
6,142,964 A 11/2000 Gilmour
6,142,965 A 11/2000 Mathewson
6,155,994 A 12/2000 Hubbard et al.
6,179,747 B1 1/2001 Kelley
6,179,800 B1 1/2001 Torrens
6,184,797 B1 2/2001 Stark et al.
6,196,956 B1 3/2001 Brown
6,228,044 B1 5/2001 Jensen et al.
6,267,742 B1 7/2001 Krivosha et al.
6,296,595 B1 10/2001 Stark et al.
6,371,123 B1 4/2002 Stark et al.
6,384,755 B1 5/2002 Hayden
6,409,691 B1 6/2002 Dakin et al.
6,436,058 B1 8/2002 Krahner et al.
6,485,447 B1 11/2002 Lavery et al.
6,491,694 B1 12/2002 Orsak
6,502,577 B1 1/2003 Bonutti
6,503,213 B2 1/2003 Bonutti
6,505,381 B1 * 1/2003 Thomson et al. ............... 16/302
6,506,172 B1 1/2003 Hepburn et al.
6,509,659 B1 1/2003 Carroll et al.
6,572,571 B2 6/2003 Lowe
6,575,926 B2 6/2003 Bonutti
6,599,255 B2 7/2003 Zhang
6,599,263 B1 7/2003 Bonutti et al.
6,637,429 B2 10/2003 Mundrick et al.
6,682,497 B2 1/2004 Jensen et al.
6,743,187 B2 6/2004 Solomon
6,770,047 B2 8/2004 Bonutti
6,890,285 B2 5/2005 Rahman et al.
6,921,377 B2 7/2005 Bonutti
6,929,616 B2 8/2005 Bonutti et al.
6,958,048 B2 10/2005 Bonutti
6,974,431 B2 12/2005 Jensen
7,101,347 B2 9/2006 Culhane et al.
7,112,179 B2 9/2006 Bonutti et al.
7,182,738 B2 2/2007 Bonutti et al.
7,204,814 B2 4/2007 Peles
7,306,573 B2 12/2007 Bonutti
7,404,804 B2 7/2008 Bonutti
7,473,234 B1 1/2009 Weltner et al.
7,517,330 B2 4/2009 Deharde et al.
2001/0047209 A1 11/2001 Solomon
2002/0029784 A1 3/2002 Stark
2002/0183655 A1 12/2002 Zhang
2003/0120183 A1 6/2003 Simmons
2004/0153010 A1 * 8/2004 Bonutti et al. .................... 601/5
2004/0215120 A1 10/2004 Jensen
2006/0036205 A1 2/2006 Bonutti
2006/0241539 A1 10/2006 Agrawal et al.
2007/0038161 A1 2/2007 Bonutti et al.
2007/0055190 A1 3/2007 Bonutti et al.
2007/0100267 A1 5/2007 Bonutti et al.
2007/0135738 A1 6/2007 Bonutti et al.
2007/0197605 A1 8/2007 Glombik et al.
2007/0219475 A1 9/2007 Bonutti et al.
2007/0219476 A1 9/2007 Bonutti et al.
2008/0091132 A1 4/2008 Bonutti

FOREIGN PATENT DOCUMENTS

DE 405327 10/1924
DE 2829562 1/1980
DE 8806231.7 5/1988
EP 0181668 5/1986
EP 0181688 5/1986
EP 0380060 1/1990
EP 0510840 10/1992
FR 2661333 4/1990

(56) References Cited

FOREIGN PATENT DOCUMENTS

| | | | |
|---|---|---|---|
| JP | 4261657 | | 9/1992 |
| JP | 2001 087296 | | 4/2001 |
| SU | 1158195 | | 5/1985 |
| SU | 1426580 | | 9/1988 |
| SU | 1671296 | | 8/1991 |
| WO | WO 88/04543 | | 6/1988 |
| WO | WO 2004/073143 | | 1/2004 |
| WO | WO 2005/086741 | | 9/2005 |
| WO | WO 2007/051168 | | 5/2007 |
| WO | WO 2007/109638 | | 9/2007 |
| WO | WO 2008/036895 | | 8/2008 |
| WO | WO 2009/111378 | A2 | 9/2009 |
| WO | PCT/US2009/035669 | | 10/2009 |

OTHER PUBLICATIONS

Advertising materials from the Internet on Jun. 5, 1998 entitled: "Ultraslingtm by DonJoy".

Neporent et al. "Weight Training for Dummies" 1997, p. 294.

Dynasplint Systems Inc., "Practitioner Information for Dynasplint LPS Orthosis—Knee Extension", date known but prior to Aug. 23, 1991.

Publication by UE Tech, Technology Meeting Human Needs, Rehabilitation Product Catalog, vol. 7, publication date unknown, but prior to Oct. 13, 1998.

Taber's Cyclopedic Medical Dictionary 16th Edition (1989) (#34), p. 521, definition of "distraction".

Joint Active Sytems, Inc., JAS; The Proven Approach to Restoring ROM (online), Copyright 2004 www.jointactivesystems.com.

* cited by examiner

SHOULDER ROM ORTHOSIS

CROSS REFERENCE TO RELATED APPLICATIONS

This application claims the benefit of priority to U.S. Provisional Application Ser. No. 61/033,716, filed Mar. 4, 2008, the contents of which are hereby incorporated by reference in their entirety.

FIELD OF THE INVENTION

The invention relates to an adjustable orthosis for stretching tissue in the human body. The invention relates to an adjustable orthosis which utilizes the principle of stress relaxation, and possibly creep, for stretching tissue such as ligaments, tendons or muscles around a joint during flexion or extension of the joint. In another aspect, the invention relates to controlling a rotation of a force imparting assembly. In a further aspect, the invention relates to supporting the scapula of the patient's body during therapy.

BACKGROUND OF THE INVENTION

In a joint, the range of motion depends upon the anatomy and condition of that joint and on the particular genetics of each individual. Many joints primarily move either in flexion or extension, although some joints also are capable of rotational movement in varying degrees. Flexion is to bend the joint and extension is to straighten the joint; however, in the orthopedic convention some joints only flex. Some joints, such as the knee, may exhibit a slight internal or external rotation during flexion or extension. Other joints, such as the elbow or shoulder, not only flex and extend but also exhibit more rotational range of motion, which allows them to move in multiple planes. The elbow joint, for instance, is capable of supination and pronation, which is rotation of the hand about the longitudinal axis of the forearm placing the palm up or the palm down. Likewise, the shoulder is capable of a combination of movements, such as abduction, internal rotation, external rotation, flexion and extension.

Most people do not appreciate the complexity of joint motion until something goes wrong, such as when an injury results in lost range of motion. When a joint is injured, either by trauma or by surgery, scar tissue can form or tissue can contract and consequently limit the range of motion of the joint. For example, adhesions can form between tissues and the muscle can contract itself with permanent muscle contracture or tissue hypertrophy such as capsular tissue or skin tissue. Lost range of motion may also result from trauma, such as excessive temperature (e.g., thermal or chemical burns), or surgical trauma, so that tissue planes which normally glide across each other may become adhered together, markedly restricting motion. The adhered tissues may result from chemical bonds, tissue hypertrophy, proteins such as Actin or Myosin in the tissue, or simply from bleeding and immobilization. It is often possible to mediate, and possibly even correct this condition by use of a range-of-motion (ROM) orthosis, but the longer the period of stiffness or loss of motion the greater the time interval and the force required to regain lost range of motion. Therefore, it is beneficial to treat the tissue or joint as early as possible. For example, a ROM orthosis may be applied immediately after surgery or as soon as the stiffness problem is diagnosed.

ROM orthoses are used during physical rehabilitative therapy to increase the range-of-motion of a joint. Additionally, they also may be used for tissue transport, bone lengthening, stretching of skin or other tissue, tissue fascia, and the like. When used to treat a joint, the device typically is attached on opposite members of the joint so that is can apply a force to move the joint in opposition to the contraction.

A number of different configurations and protocols may be used to increase the range of motion of a joint. For example, stress relaxation techniques may be used to apply variable forces to the joint or tissue while in a constant position. "Stress relaxation" is the reduction of forces, over time, in a material that is stretched and held at a constant length. Relaxation occurs because of the realignment of fibers and elongation of the material when the tissue is held at a fixed position over time. Treatment methods that use stress relaxation are serial casting and static splinting. One example of devices utilizing stress relaxation is the Joint Active System, which uses a rack and pinion gear to move and hold the joint in a constant position.

Sequential application of stress relaxation techniques, also known as Static Progressive Stretch ("SPS") uses the biomechanical principles of stress relaxation to restore range of motion (ROM) in joint contractures. SPS is the incremental application of stress relaxation—stretch to position to allow tissue forces to drop as tissues stretch, and then stretching the tissue further by moving the device to a new position—repeated application of constant displacement with variable force. In an SPS protocol, the patient is fitted with an orthosis about the joint. The orthosis is operated to stretch the joint until there is tissue/muscle resistance. The orthosis maintains the joint in this position for a set time period, for example five minutes, allowing for stress relaxation. The orthosis is then operated to incrementally increase the stretch in the tissue and again held in position for the set time period. The process of incrementally increasing the stretch in the tissue is continued, with the pattern being repeated for a maximum total session time, for example 30 minutes. The protocol can be progressed by increasing the time period, total treatment time, or with the addition of sessions per day. Additionally, the applied force may also be increased.

Exemplary orthoses that utilize the stress relaxation and/or SPS protocols include, but are not limited to, those described in U.S. Pat. No. 6,921,377 ("Finger Orthosis"), U.S. Pat. No. 6,770,047 ("Method of using a neck brace"), U.S. Pat. No. 6,599,263 ("Shoulder Orthosis"), U.S. Pat. No. 6,113,562 ("Shoulder Orthosis"), 6,503,213 ("Method of using a neck brace"), U.S. Pat. No. 6,502,577 ("Finger Orthosis"), U.S. Pat. No. 5,848,979 ("Orthosis"), U.S. Pat. No. 5,685,830 ("Adjustable Orthosis Having One-Piece Connector Section for Flexing"), U.S. Pat. No. 5,611,764 ("Method of Increasing Range of Motion"), U.S. Pat. No. 5,503,619 ("Orthosis for Bending Wrists"), U.S. Pat. No. 5,456,268 ("Adjustable Orthosis"), 5,453,075 ("Orthosis with Distraction through Range of Motion"), U.S. Pat. No. 5,395,303 ("Orthosis with Distraction through Range of Motion"), U.S. Pat. No. 5,365,947 ("Adjustable Orthosis"), U.S. Pat. No. 5,285,773 ("Orthosis with Distraction through Range of Motion"), U.S. Pat. No. 5,213,095 ("Orthosis with Joint Distraction"), and U.S. Pat. No. 5,167,612 ("Adjustable Orthosis"), and U.S. Pat. No. 7,182,738 ("Patient monitoring apparatus and method for orthosis and other devices"), all to Bonutti and herein are expressly incorporated by reference in their entirety. It should be noted that the SPS protocol is disclosed in a number of the above-identified patents. It should be further noted that the mark STATIC PROGRESSIVE STRETCH COMPANY is a registered trademark of Joint Active Systems, Inc (Effingham, Ill.).

Another treatment protocol uses principles of creep to apply a constant force over variable displacement. In other words, techniques and devices utilizing principles of creep involve continued deformation with the application of a fixed load. For tissue, the deformation and elongation are continuous but slow (requiring hours to days to obtain plastic deformation), and the material is kept under a constant state of stress. Treatment methods such as traction therapy and dynamic splinting are based on the properties of creep.

One potential disadvantage of using a static load, however, is that the amount of force needed to effect tissue stretching or creep may change over time. For instance, while a 10 lb force may initially provide desirable results in the beginning of the treatment protocol, it may be insufficient after the tissue has begun to stretch. Likewise, the amount of force needed in the beginning of the treatment protocol may be too much force for use in later stages of the protocol.

Exemplary orthoses utilizing the creep protocol include U.S. Pat. Nos.; 5,167,612, 5,365,947, and 5,456,268 entitled "Adjustable Orthosis", and U.S. Pat. No. 5,685,830 entitled "Adjustable Orthosis having one-piece connector section for flexing" all to Bonutti; U.S. Pat. No. 6,413,231, entitled "Device To Assist In Therapy Of Patient Who Has Limited Jaw Opening;" U.S. Pat. No. 5,645,521, entitled "Shoulder Physical Therapy Device;" U.S. Pat. No. 5,070,868, entitled "Adjustable Splint;" and U.S. Pat. No. 4,947,835, entitled "Adjustable splint assembly;" all to assigned to Dynasplint System Inc. and all of which herein are expressly incorporated by reference in their entirety. Another example of orthoses utilizing the creep protocol include U.S. Pat. No. 5,472, 410 to Hammersly, entitled "Adjustable Flexion and Extension Joint Orthoses," and U.S. Pat. No. 5,437,619 to Malewicz et al., entitled "Range-of-Motion Splint with Eccentric Spring," both of which are expressly incorporated by reference in their entirety.

In the past, treatment protocols and related devices utilized either stress relaxation or creep, but not both.

SUMMARY OF THE INVENTION

The invention, in one aspect, is directed to devices and methods of using a combination of stress relaxation and creep protocols to treat contractures. Without being bound to a particular theory, it is believed that combining these loading conditions, such as by applying them in a Static Progressive Stretch mode, may reduce the overall treatment time or may improve the overall amount of tissue stretch achieved.

One embodiment of the invention relates to a device for stretching tissue around a joint between two pivotable or rotatable body portions near a joint. The device has two frame brackets that are connectable to the body portions near their joint. A drive assembly is used to move one frame bracket relative to the other so that the secured body portions may be moved, for instance, from a first position to a second position. The drive assembly also may be capable of moving the body portion to third, fourth, or even more positions or configurations.

In another embodiment, two pivotable and or rotatable frame bracket portions provide for stretching and positioning of two joints, such as adjacent joints of the elbow and shoulder.

A force application assembly associated with the frame brackets then imparts forces to one or more of the body portions. The force application assembly cooperates with the frame brackets to thereby exert a force upon the jointed body portions, and may include one or more springs, such as a linear spring, leaf spring, helical spring, torsional spring, or the like, or a resilient cord or cable, that help impart a force on the patient's body. Alternatively, the force application assembly may use a fluid bladder or otherwise have resilient material that imparts forces on the body.

The force application assembly also could impart a dynamic tension, which continues to apply a force after the device is adjusted to a set position. The dynamic tension could be a known spring or resilient cord, string, wire or cable, which can have adjustable control to vary the force, or could have a control knob or electrical control, and could be responsive to a sensor. Springs and other components used in the invention may be formed of low-cost polymeric materials so that all or part of the device may be designed to be economically disposable. In addition, the force application assembly may have an adjustable controllable dynamic system that allows electrical feedback or compliance monitoring of the system. Some examples of feedback or monitoring systems that may be used with the invention are described in U.S. Pat. No. 7,182,738 entitled "Patient Monitoring Apparatus and Method for Orthosis and Other Devices" to Bonutti et al., the entirety of which is incorporated herein by reference.

The forces imparted to the body may be substantially constant, or alternatively may vary in degree, force profile, or duration. The device may hold the pivotable and or rotational frame brackets in any of its positions for a predetermined period of time, until a desired amount of tissue stretch relaxation or creep is achieved, or until some other parameter is met. In some embodiments, one or more cuffs are used to attach one or more frame brackets to the patient's body, as in a limb or limb portion of a body. Depending on the desired treatment, a cuff and force application assembly may be configured to impart torsional forces on one of the body portions instead of, or in addition to, imparting bending forces. Axial forces may also be applied either alone or in combination with other types of forces.

The invention also is directed to methods of increasing the range of motion of connective tissue between adjacent body portions interconnected by a joint. In particular, one embodiment of the invention involves connecting a first and second frame bracket with a first and second body portion, respectively. One of the frame brackets may then be moved from a first position to a second position relative to another frame bracket, utilizing the principles of stress relaxation to stretch the tissue about the joint. While in this second position, a force may be imparted on a body member to urge it to move even further than the second position, utilizing the principles of creep to further stretch the tissue about the joint. This force may be applied throughout a treatment interval, or may vary in degree, force profile, or duration. Some embodiments involve moving the body member to third, fourth or even more positions. These multiple positions may gradually increase in a particular direction or range to account for stretching of the body tissue.

In accordance with the invention, the drive assembly includes a drive shaft, rotated by hand or an actuator, to set a position of the device. Static or dynamic tensioning is achieved by rotating the drive shaft, which operates to impart a force to the device, for the therapeutic benefit of the patient.

A rotational position of the drive shaft is maintained by a rotation control device, which enables an operator to rotate the drive shaft to adjust a tension of the device, and concomitantly prevents rotation of the drive shaft incident to forces imparted by a load. Loading forces include, for example, gravitational forces acting upon the body, or body tissue resisting stretching.

The rotation control subassembly includes an inner and an outer race defining a space therebetween, and rotatable elements, such as pins or spheres, disposed within the space. When one race is rotated with respect to another, the pins are urged along a ramp associated with one of the races, whereby the pins become pinched and bind between the inner and outer races, thereby preventing further movement of one race relative to another. Ramps are provided for both possible directions of rotation. One race is fixed against rotation, whereby when the raceways become fixed relative to each other, neither raceway rotates with respect to the device.

The drive shaft is connected to a series of engagement dogs, which are additionally interposed between the inner and outer raceways. When the drive shaft is rotated, bosses associated with the dogs engage cams associated with one of the raceways, whereby the drive shaft operates to rotate, or drive the raceway. The engagement dogs simultaneously impinge upon the pins or spheres between the raceways, enabling free rotation of the drive shaft by ensuring that the pins do not travel sufficiently far along the ramp to cause the inner and outer raceways to bind.

A lever, associated with the driven raceway, is operated when the drive shaft is rotated, and causes a tensioning member to tighten or loosen as the drive knob is rotated. In one embodiment, the lever is a spool, and the tensioning member is a cable.

BRIEF DESCRIPTION OF THE DRAWINGS

A more complete understanding of the invention, and the attendant advantages and features thereof, will be more readily understood by reference to the following detailed description when considered in conjunction with the accompanying drawings wherein.

DETAILED DESCRIPTION OF THE INVENTION

The invention relates to a ROM device for stretching tissue, such as the connective tissue around a joint, between at least a first and second body portion, in one aspect of the invention, utilizing the principles of stress relaxation, and possibly also creep. As previously identified, treatment protocols based on principles of creep involve continued tissue movement and deformation under the application of constant loading, while treatment protocols based on principles of stress relaxation involve varying loading and constant displacement. Techniques utilizing principles of creep therefore allow joint position to change over time as tissue stretches in response to the applied load, whereas techniques utilizing stress relaxation maintain a constant joint position while allowing the applied load to vary over time—usually to diminish or lessen as the tissue stretches. Relaxation occurs because of the realignment of fibers and elongation of the material when the tissue is held at a fixed position over time. As explained in greater detail below, the invention also utilizes the principles of Static Progressive Stretch to provide a sequential application of stress relaxation and, possibly also creep, to the treated tissue. Using the following detailed description and examples, skilled artisans will recognize that it is possible to modify currently existing devices to include features of the invention. Concepts applicable to the instant invention are disclosed for example in related U.S. Pat. Nos. 6,113,562, 6,599,263, 6,929,616 and 7,112,179, and 7,452,342, as well as U.S. Patent Publication No.'s 2004/0153010 and 2007/0038161, to Bonutti, et al., all of which are incorporated by reference herein.

A joint and the first and second body portions can define on one side (the flexor side) of the joint an inner sector which decreases in angle as the joint is flexed (bent) and on the opposite side (the extensor side) of the joint an outer sector which decreases in angle as the joint is extended (straightened). The orthosis of the invention is affixable to either the flexor or extensor side of the joint for treatment of flexion or extension contractures. In flexion and extension the joint may also exhibit slight internal or external rotations. As noted above, some joints may also be capable of even greater rotation. While the examples discussed herein primarily illustrate aspects of the invention in the context of increasing range of motion for flexion and extension, they also may be used to increase rotational range of motion.

Figure 19:
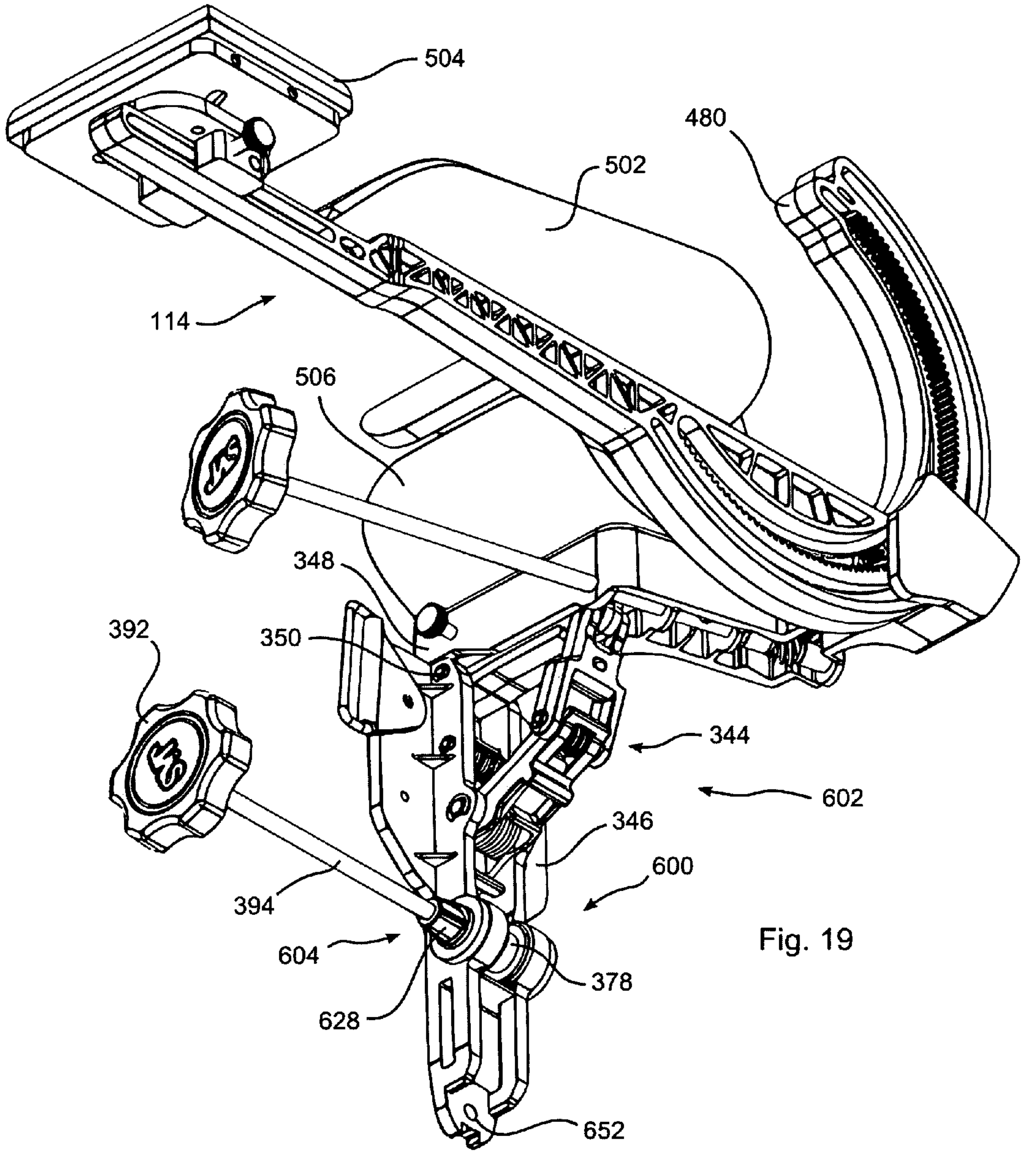
FIG. 19 is perspective view of a portion of an orthosis device, including the rotation control device of FIG. 17.

The orthosis includes, in one embodiment in accordance with the invention, a drive assembly 600 (FIG. 19) for moving the second body portion with respect to the first body portion from a first position to a second position. The orthosis fully or at least partially restricts motion of the second body portion in at least one direction (e.g. flexion, extension, or rotation), utilizing the principles of stress relaxation to stretch the tissue around the joint.

The orthosis further comprises a force application assembly 602 that can apply loading to the tissue while the device is in one or more of its angular positions. The force applied by the force application assembly 602 preferably is in a direction where joint or tissue movement is not fully restricted by the drive assembly 600 or other components of the device. As explained below, the force application assembly 602 can provide a constant force to the second body portion, may be capable of permitting adjustment of the force applied to the second body portion, or may be configured to provide a varying force profile across the second body portion.

Initially, the force applied by the force application assembly 602 may be less than the force applied by the drive assembly 600. As the force in the tissue drops, however, the drive assembly 600 force may reduce to a point where the force application assembly 602 provides a greater force on the tissue. The application of the force application assembly 602 force results in a continuous stretching of the tissue around the joint, maintaining, decreasing, or preventing a relaxation of the tissue. When a resilient cord or other resilient force transferring member is used, the drive assembly 600 and force application assembly 602 may together take advantage of principles of both stress relaxation and creep.

After a set time period, the drive assembly 600 may be used to move the second body portion from the second position to a third position, incrementally stretching the tissue surrounding the joint. Thus, the orthosis may be capable of moving from a first position to one or more other positions to provide different configuration angles of the device. It is contemplated that the drive assembly 600 may be used to incrementally move the second body portion after the expiration of a predetermined time or until completion of the protocol. This approach is different from application of a constant load over a sustained time period.

Alternatively, the orthosis of the invention can be used to effect rotational movement between bones in a body of a patient. For example, in the forearm it may be desirable to stretch viscoelastic body tissue connected with the ulna and radius bones and/or with the humerus in the arm of a patient in order to obtain a greater range of supination or pronation. During supination or pronation of a hand of a patient, the ulna and radius bones in the lower portion of the arm of the patient move relative to each other.

The drive assembly 600 of the orthosis may be used to move the radius bones with respect to the ulna from a first position to a second position when in the second position. The orthosis may restrict movement of the radius bones in at least one direction, such as by preventing the radius and ulna from returning to the first position. In this manner, the drive assembly 600 utilizes the principles of stress relaxation to stretch the tissue around the wrist joint. After a set time period, the drive assembly 600 may be used to move the radius bones from the second position to a third position, incrementally stretching the tissue surrounding the wrist joint.

As previously explained, the force application assembly 602 can apply loading to the radius bones while the drive assembly 600 is in one or more positions. This allows the device to utilize the principles of creep to help stretch the tissue. Initially, the force applied by the force application assembly 602 may be less than a force applied by the drive assembly 600. As the force in the tissue drops, the drive assembly 600 force may reach a point where the force application assembly 602 provides a greater force to the tissue. The forces applied by the force application assembly 602 results in a stretching of the tissue around the joint during the set time period, maintaining, decreasing, or preventing a relaxation of the tissue.

In addition, the forces applied by the drive assembly 600 and force application assembly 602 may be in substantially the same direction or alternatively may differ. For example, increasing range of motion for a knee may involve applying loading on the joint in substantially the same direction for both assemblies. In contrast, treatment of an ankle, wrist, elbow, or shoulder may involve the drive assembly 600 applying a force to cause flexion or extension while the force application assembly 602 applies rotational forces (or vice versa).

Figure 1:
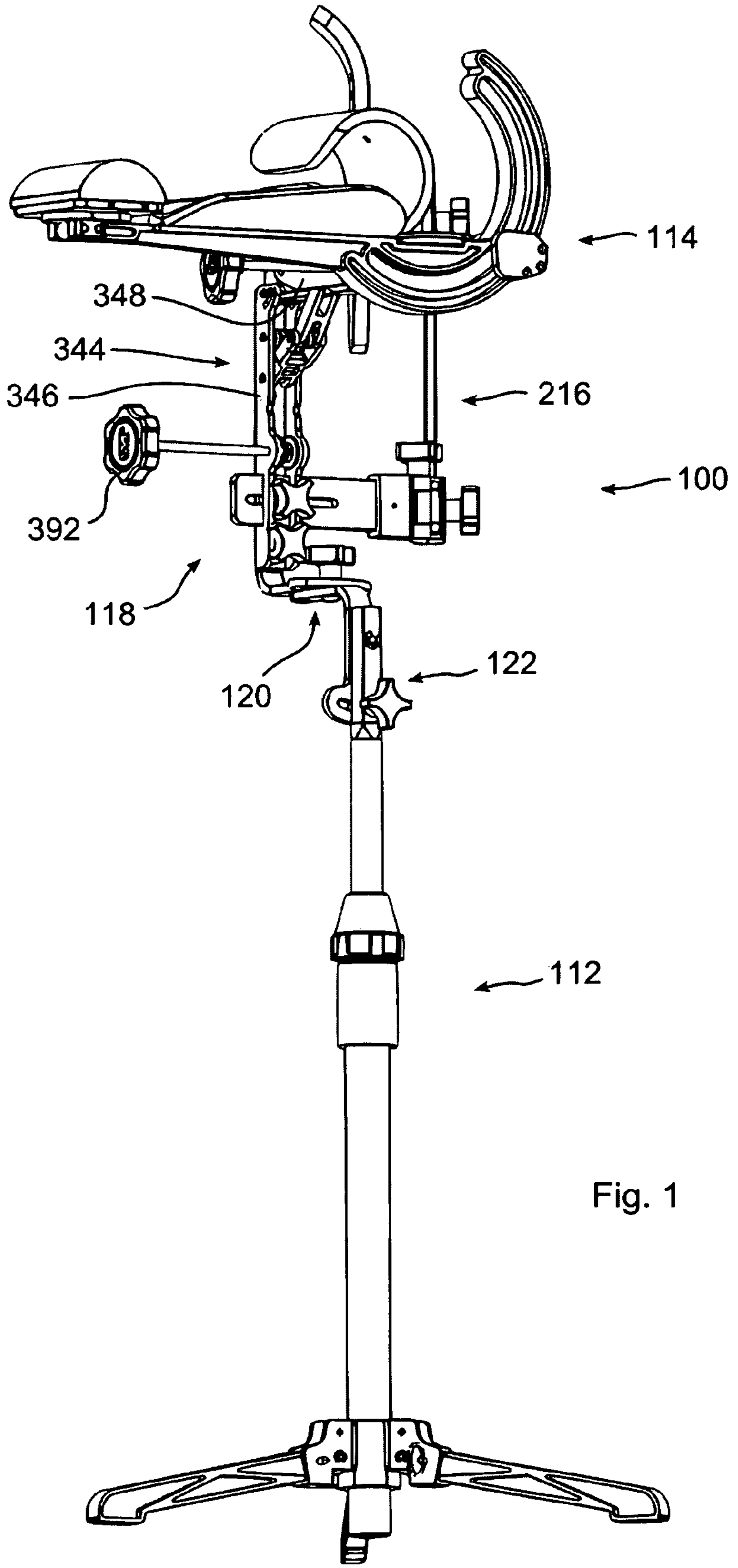
FIG. 1 is an illustration of one orthosis device in accordance with the invention.
Figure 2:
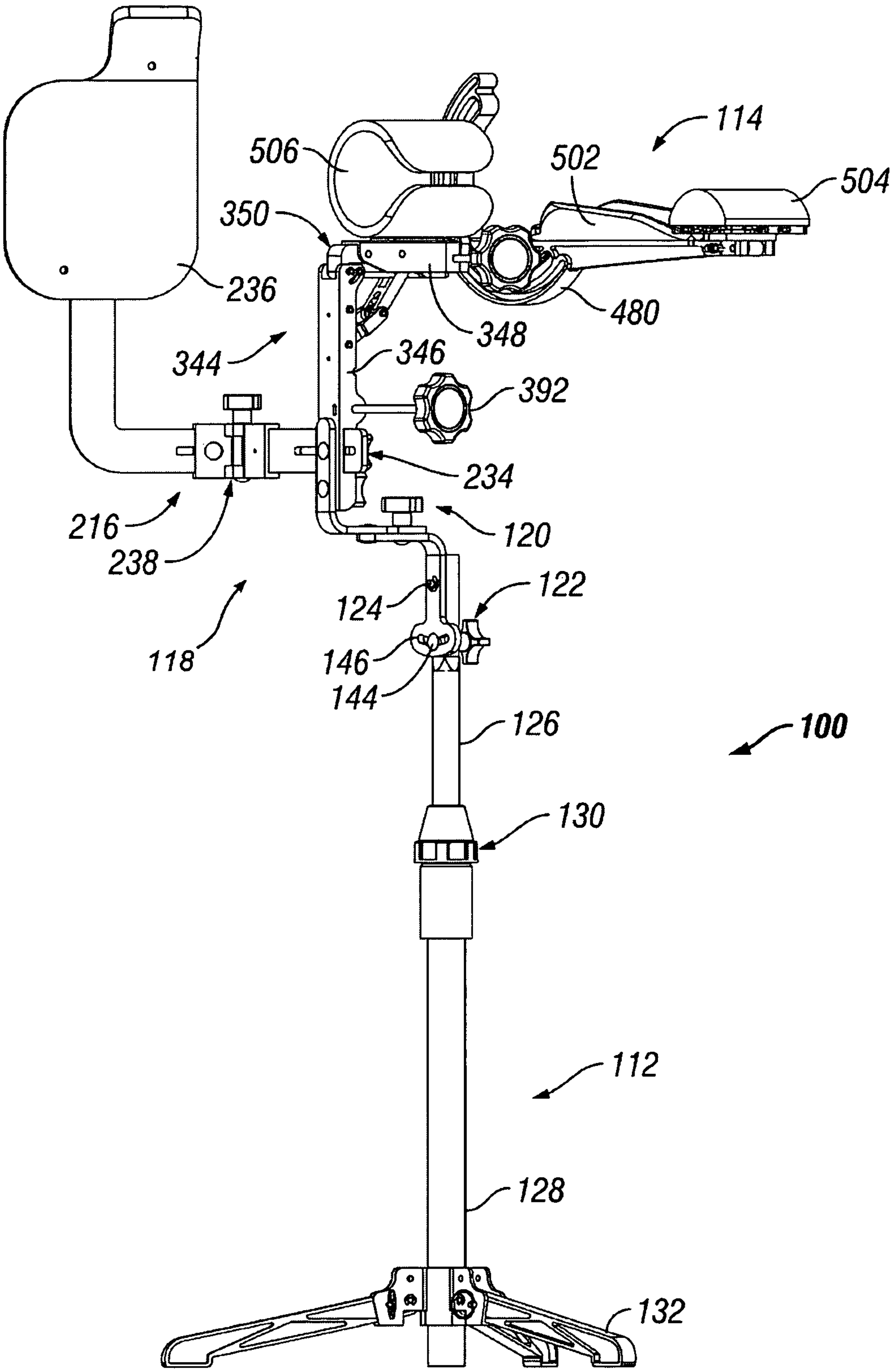
FIG. 2 is an alternative perspective of the device of FIG. 1, in a configuration corresponding to 90 degrees of abduction.

Referring now to the drawing figures in which like reference designators refer to like elements, there is shown in FIGS. 1 and 2 an orthosis device 100 having a base 112 and a limb engaging portion 114, connected to base 112. The embodiment shown is directed to therapeutic treatment of the shoulder (glenohumeral) and elbow (humeroulnar, humeroradial, proximal radioulnar) joints, although as will be apparent to one skilled in the art, the device is readily adapted to other joints of the body.

Base

Figure 3:
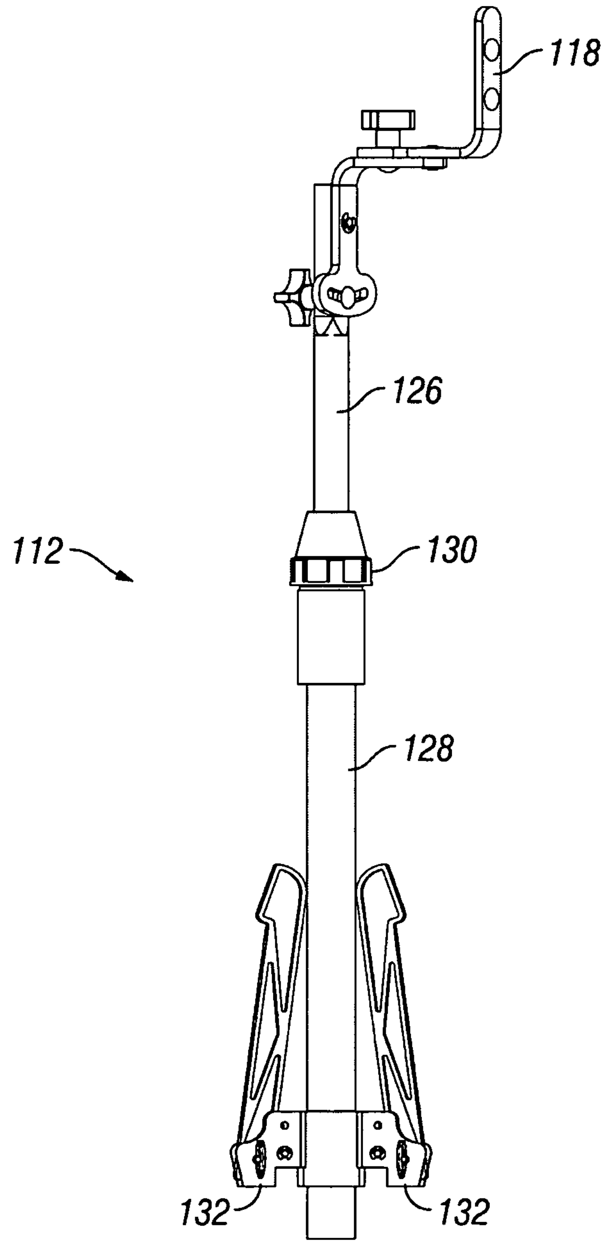
FIG. 3 depicts the base of the device of FIG. 1, with legs folded.
Figure 12:
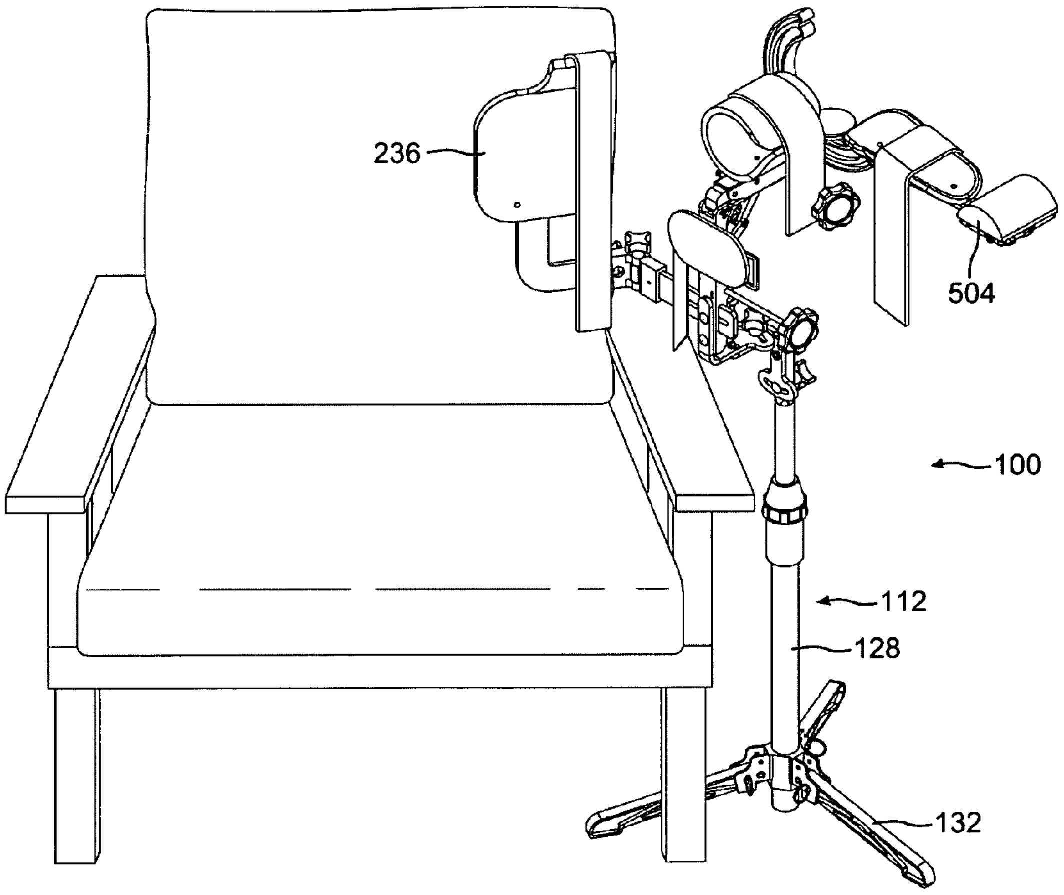
FIG. 12 illustrates a bended frame portion of a device in accordance with the invention, operative to conform to a working environment, in this illustration, a chair.
Figure 13:
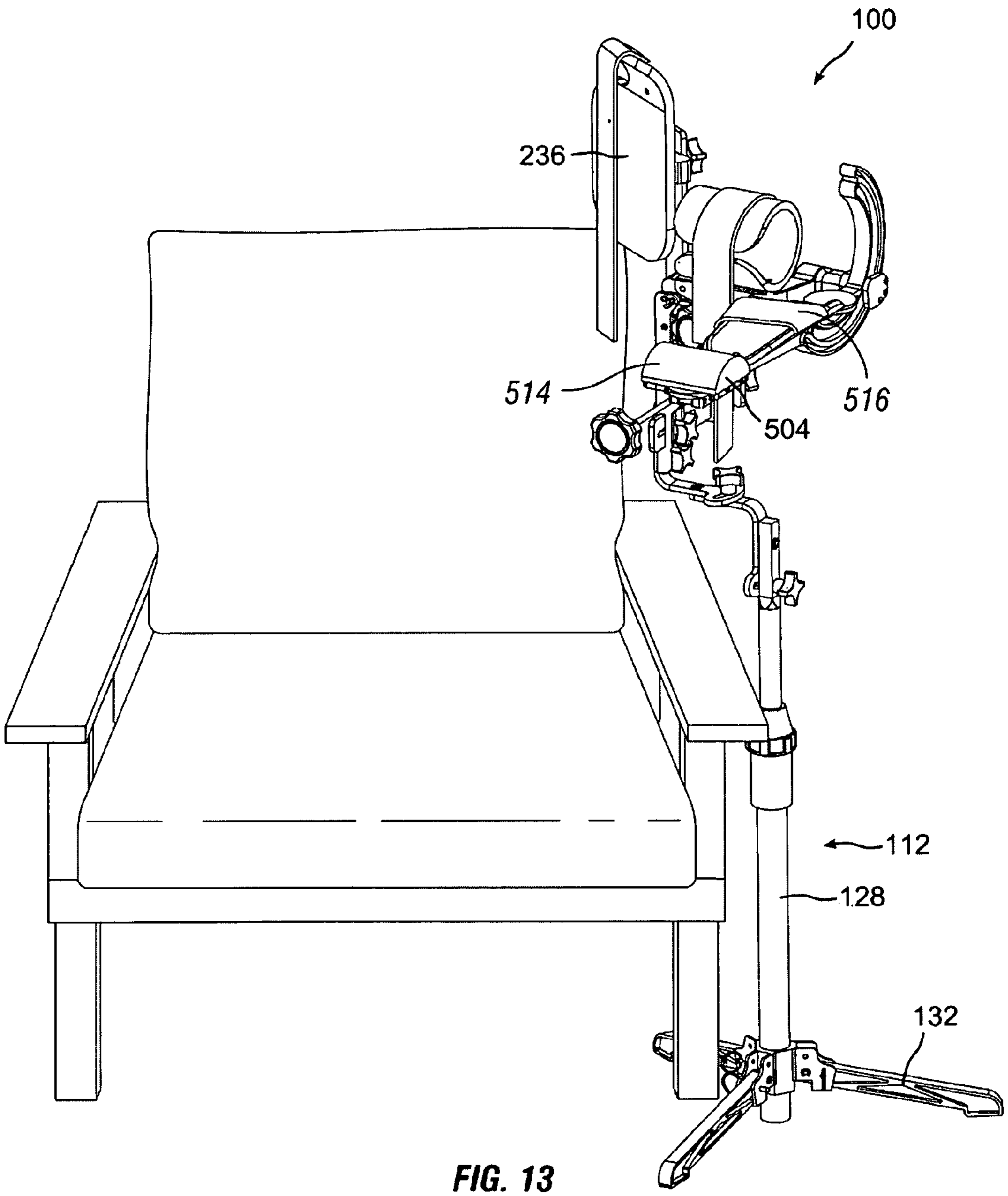
FIG. 13 illustrates an alternative view of the device of FIG. 12.

In the embodiment shown in FIGS. 1 and 2, stabilization subsection 216 is pivotally connected to frame 118, the latter pivotally connected to base 112 at adjustable connections 120, 122, permitting angular displacement of frame 118 along different planes, respectively. In particular, connection 120 enables adjustments in flexion and extension, while connection 122 enables tilting of frame 118. Frame 118 is pivotally connected to shaft 126 of base 112 at pin 124. Shaft 126 is slidably engaged to elongated base member 128, in this embodiment a tube, secured by adjustable ring collar 130, to be retained at a desired height and angular displacement with respect to a surface upon which feet 132 rest. Feet 132 pivot to a storage or transport position for convenience, as can be seen in FIG. 3. In particular, feet 132 pivot to lie alongside base member 128, thereby reducing the storage or transport profile of the base. With reference to FIGS. 12 and 13, Frame 118 is provided with a bend, wherein frame 118 may extend over a chair armrest, or may be stabilized thereby, thus better adapting the device to the working environment.

Figure 10:
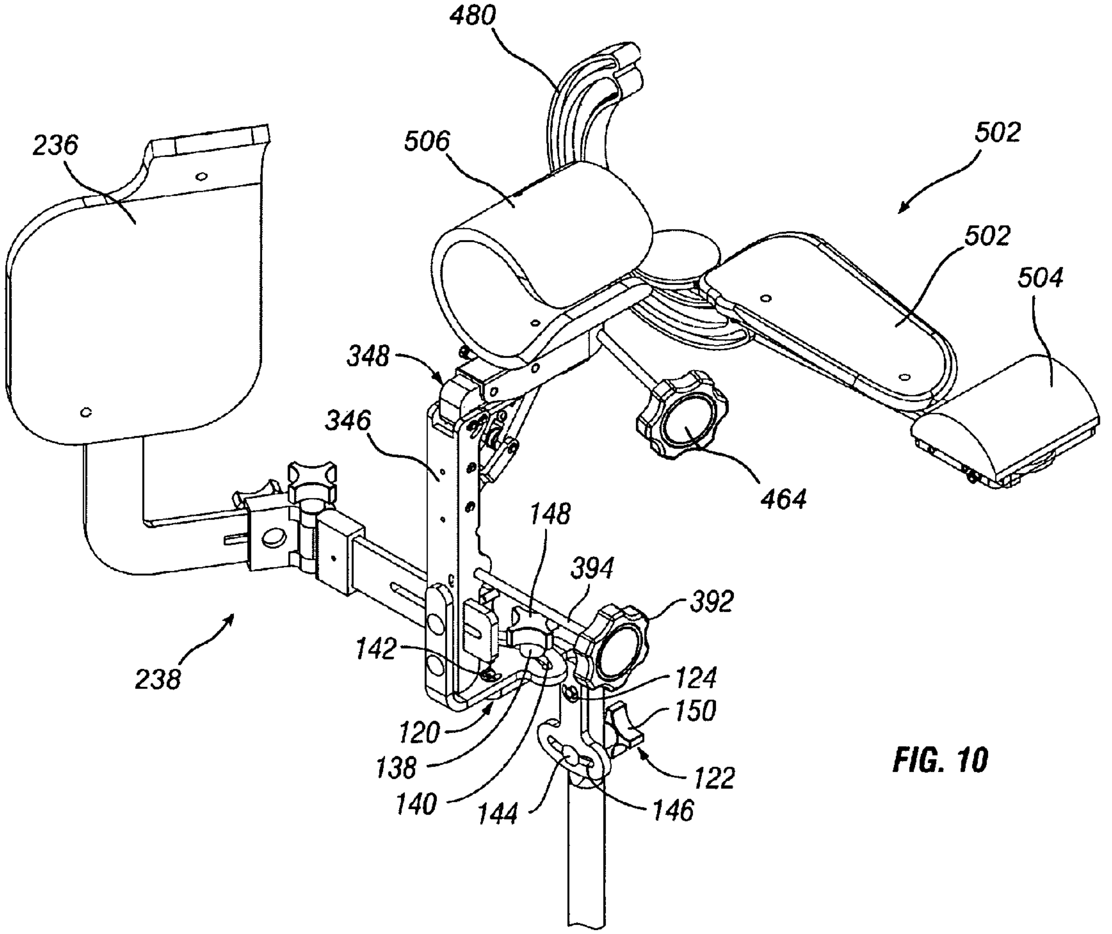
FIG. 10 is view of a portion of the device of FIG. 1.

More particularly, with reference to FIG. 10, in an embodiment in accordance with the invention, adjustable connection 120 is provided as a pin 138 in a slot 140, pivotable about a pivot pin 142, whereby a range of permissible flexion and extension may be set based upon the length of slot 140, and the offset from slot 140 to pivot pin 142. A similar adjustment mechanism is found as adjustable connection 122, which is provided with pin 144 in slot 146, pivoting about pivot pin 124. Threaded adjustment knobs 148,150 enable securing a desired adjustment for adjustable connections 120 and 122, respectively.

Figures 20, 20A:
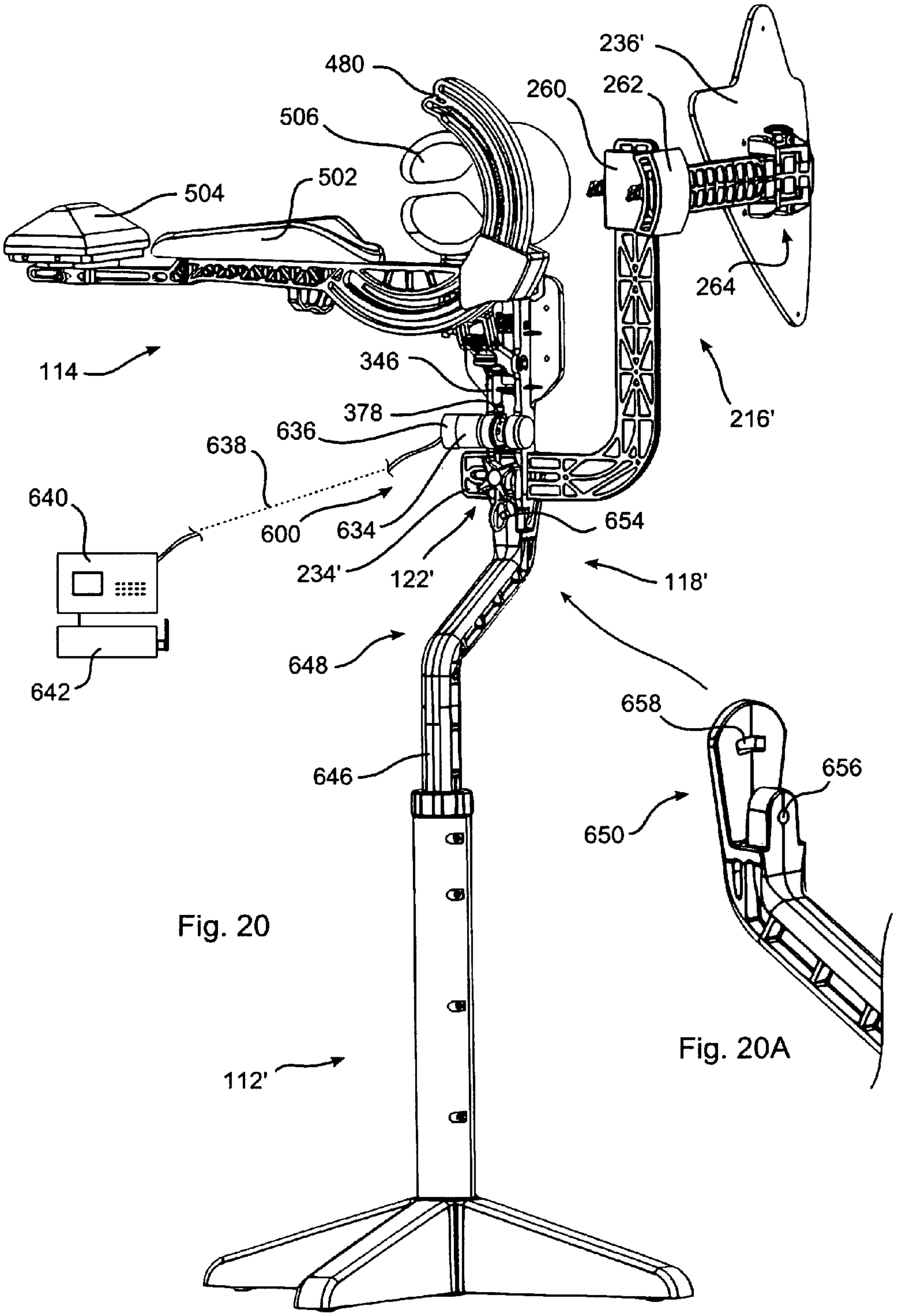
FIG. 20 is a perspective view of the orthosis device of FIG. 19, including a floor stand in accordance with the invention.
Figure 21:
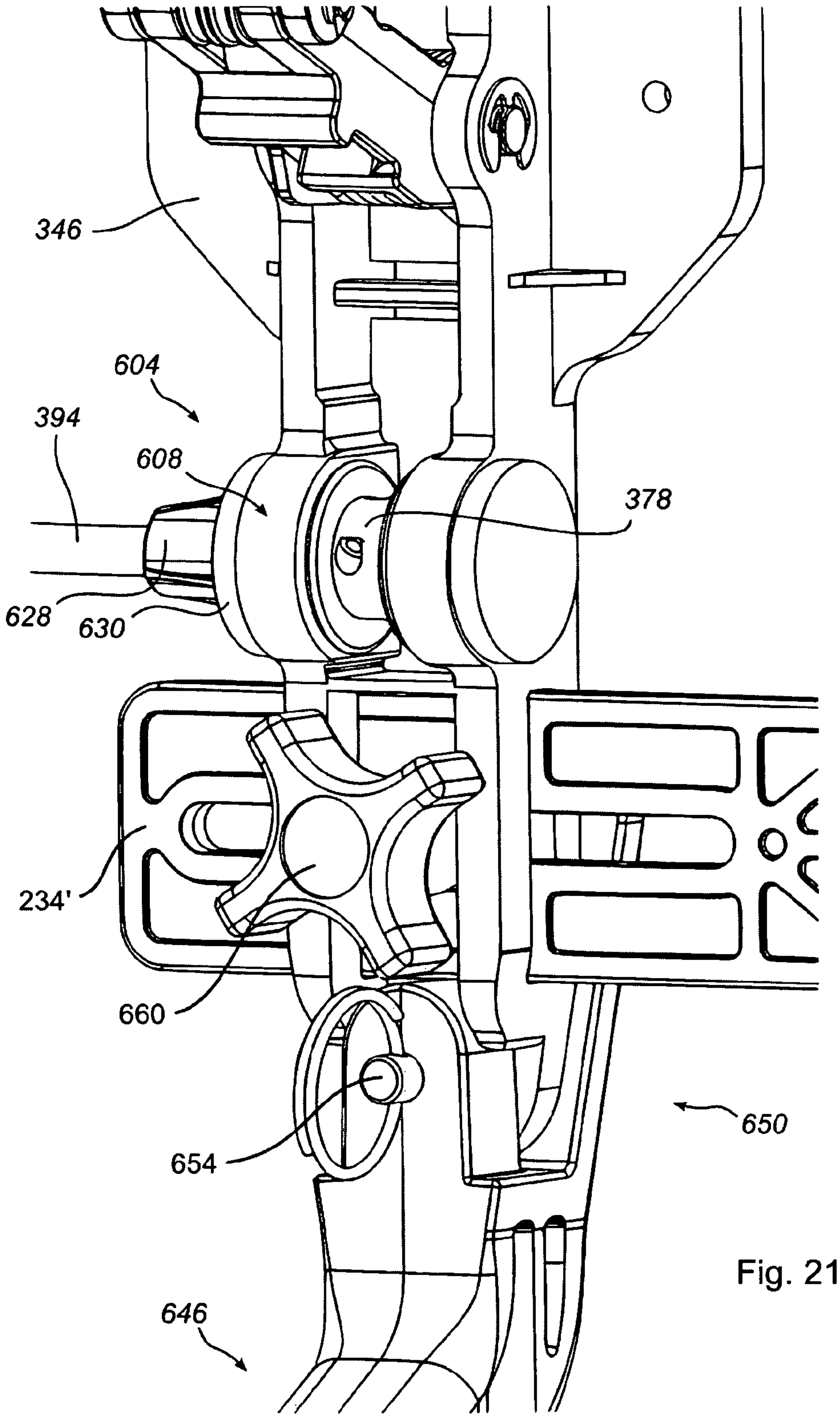
FIG. 21 is a perspective view of a connecting portion of the device of FIG. 20.

In an alternative embodiment of the invention, shown in FIGS. 20-21, frame 118' is molded or otherwise fashioned to include an offset section 648. Frame 118' comprises a sliding section 646, which telescopically engages with base 112'. Offset section 648 disposes an upright engagement section 650 in a non-collinear configuration with respect to base 112'. FIG. 20A illustrates an enlarged view of engagement portion 650 of frame 118' that engages stabilization subsection 216 or 216'. Pin 654 passes through apertures 652 and 656 in frame bracket 346 and sliding section 646, respectively, forming a pivotal connection. Set screw 660 passes through frame bracket 346 and aperture 658, secured by a threaded fastener (not shown), to maintain base 112' and subsection 216' in fixed relative position. Retaining slot 658 enables a limited angular tilt of subsection 216' with respect to base 112', which is maintained after screw 660 is tightened. FIG. 21 provides an enlarged view of a connection between offset section 648 and drive assembly 600.

Figure 23:
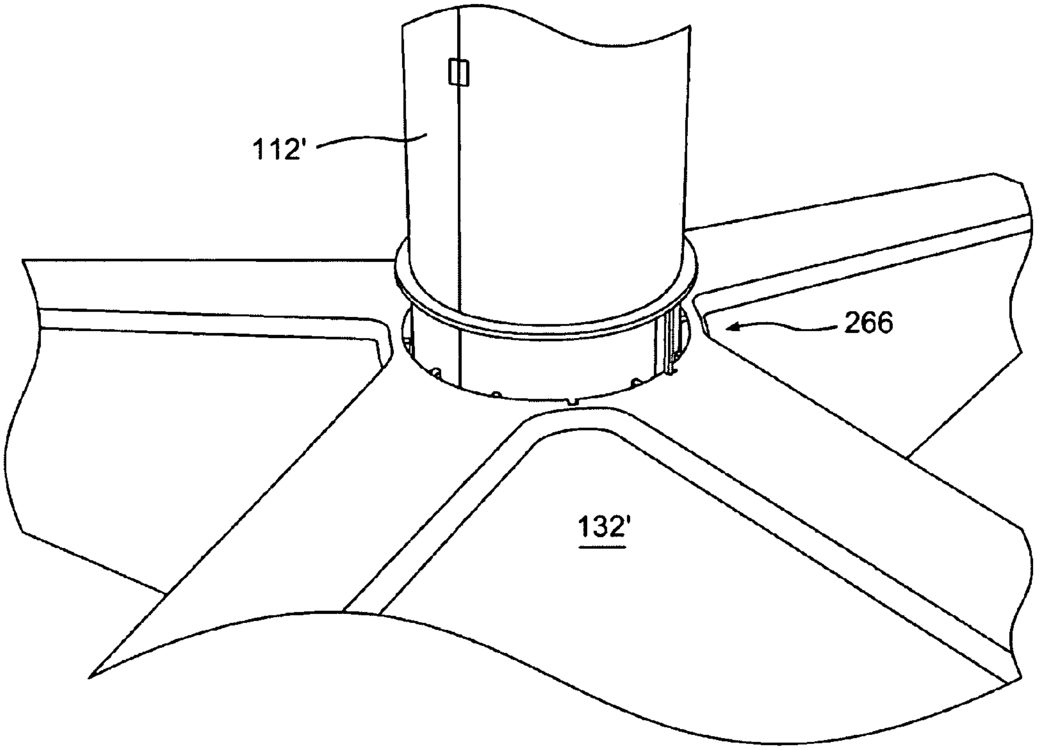
FIG. 23 is a perspective view of a connection between portions of a floor stand in accordance with the invention.

As shown in FIG. 23, a device 100 in accordance with the invention is provided with alternative feet structure 132' which are connected to base 112' in a sleeved connection. Key 266 ensures that feet 132' are positioned advantageously, and that base 112' does not rotate while device 100 is in use. A taper or other friction fit may be provided between base 112' and feet structure 132', to maintain a connection as device 100 is moved before, during, or after use.

It should be understood that while a floor mount is illustrated, other mounting devices are contemplated within the scope of the invention. Examples include a clamp or clip engageable with base 112 or 112', which enables the fastening of a device in accordance with the invention to another mounting location, for example a furnishing or other structure.

Stabilization

Figure 4:
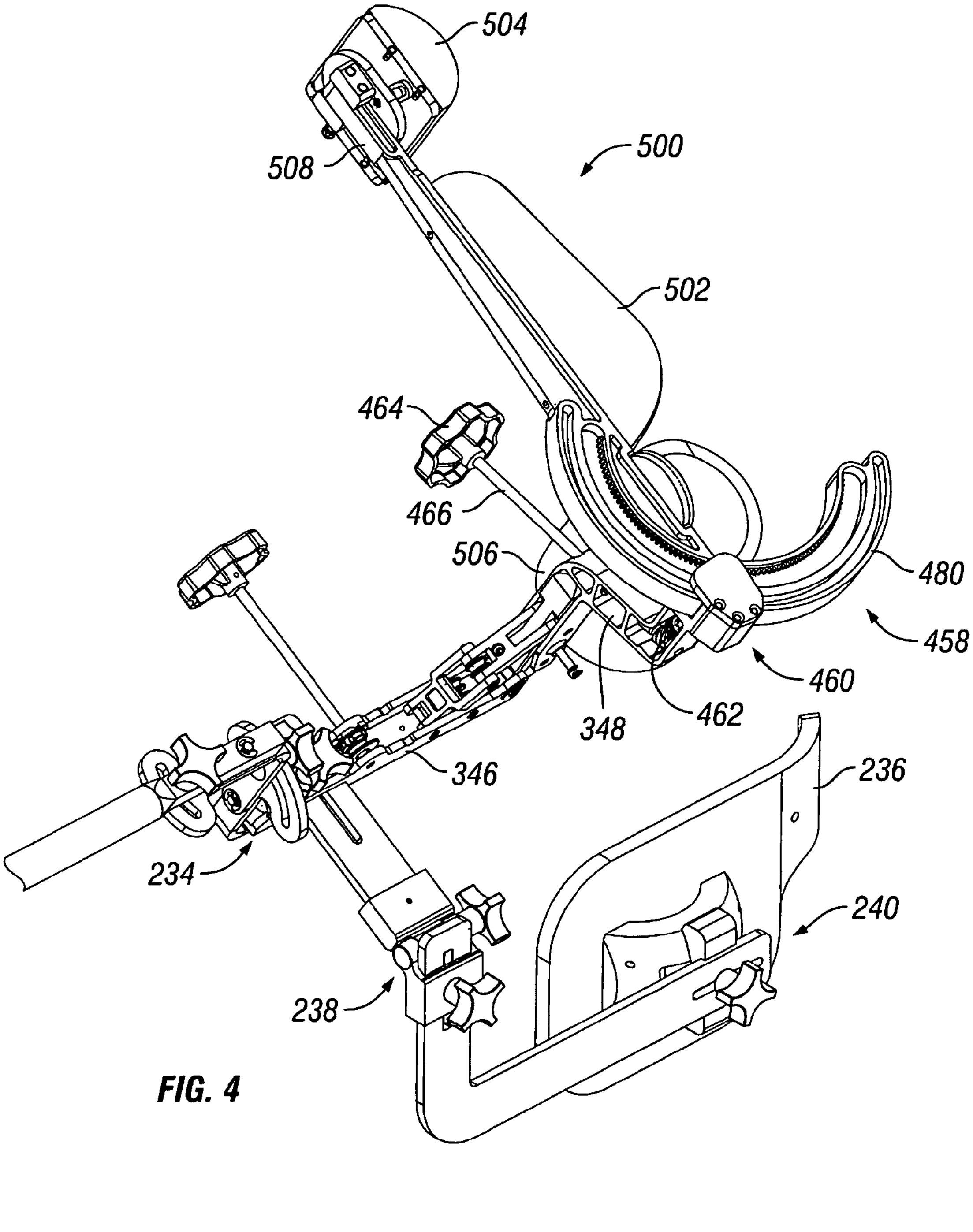
FIG. 4 depicts a portion of the device of FIG. 1, viewed from below, in a configuration corresponding to 60 degrees of flexion.

With reference to FIG. 2, a stabilization subsection 216 is provided to maintain areas adjacent to joints undergoing therapy in a relative fixed position. If not needed, subsection 216 may be removed by disengagement at sliding engagement member 234, in this embodiment a flange with an elongated slot. Alternatively, subsection 216 may be slid within engagement member 234, and rotated at adjustment member 238, to position a scapula engagement panel 236 in a supporting position with respect to a wearer's scapula. Adjustment member 238, in this embodiment a hinge, thus enables adjustment along a different plane with respect to engagement member 234. Further adjustment is enabled through adjustment arc 240, as can be seen in FIG. 4.

Stabilization subsection 216 is advantageously used to prevent unwanted movement of a patient's scapula as force is applied to joints of the arm and shoulder. In particular, a voluntary or involuntary forward rolling movement of the scapula could diminish or alter the application of therapeutic force applied to an shoulder joint, particularly for internal rotation. Similarly, should the device be employed on a leg, a correlative engagement panel can be employed to prevent unwanted movement of the back or hip.

Figure 5:
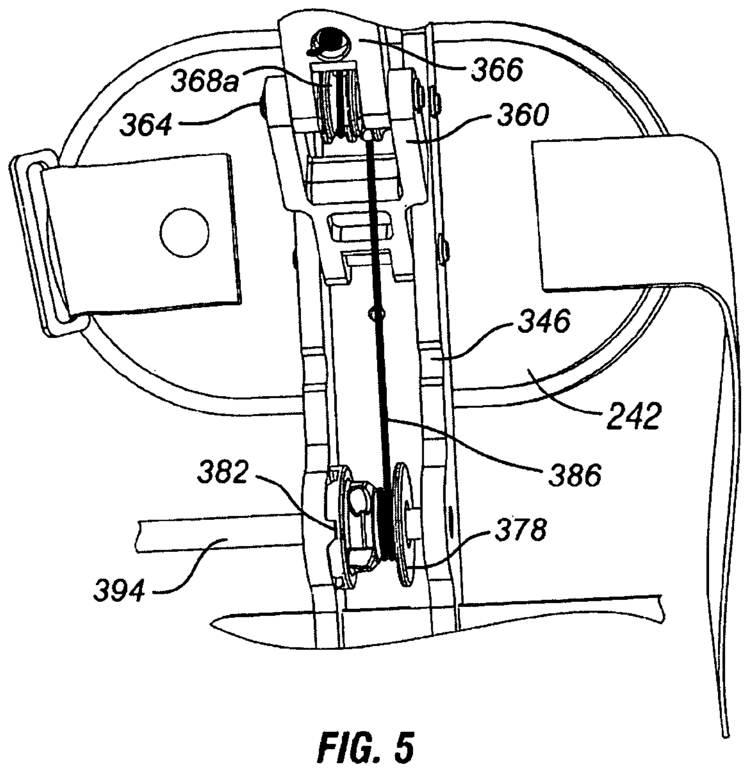
FIG. 5 depicts a detail of the device of FIG. 1, particularly a force application assembly in accordance with the invention, detailing a cable and pulley configuration.
Figure 6:
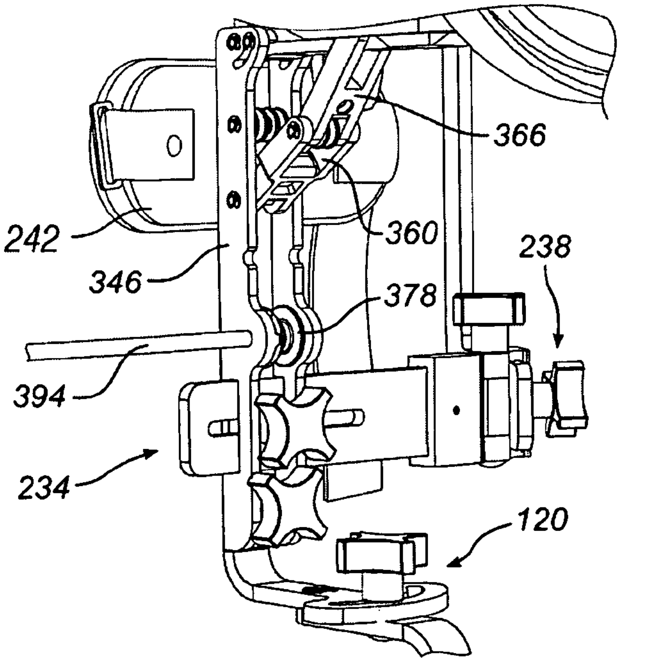
FIG. 6 is an alternative perspective of the detail of FIG. 5.

Additional stabilization members, such as side stabilization panel 242, visible for example in FIGS. 5 and 6, may be advantageously employed to maintain device 100 in a correct position, and to ensure that applied forces are directed to the target joint, along appropriate vectors.

Figure 11:
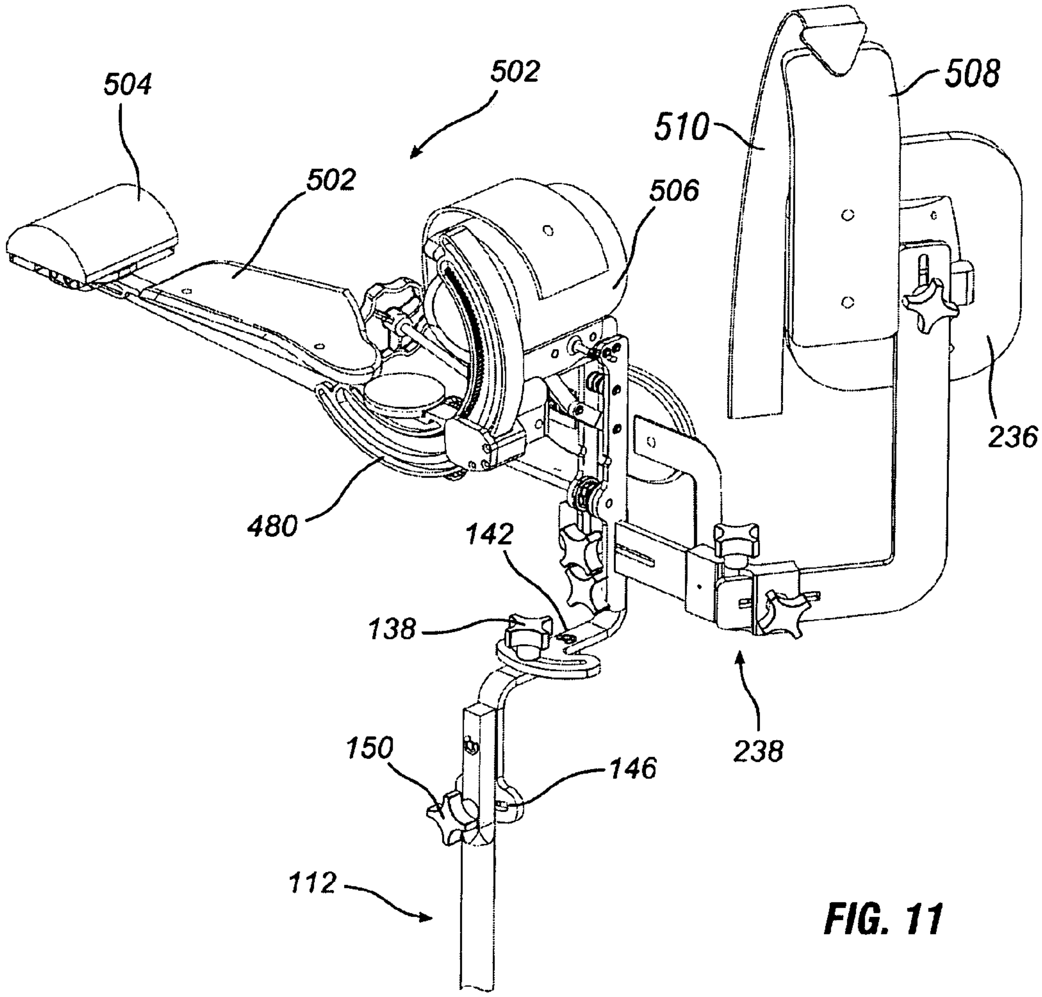
FIG. 11 illustrates a biasing member in accordance with the invention.

With reference to FIG. 11, a biasing panel 508 may be provided, cooperative with biasing strap 510, to urge the scapula into a proper position for therapy, applying a continuous force in the direction of scapula engagement panel 236. Strap 510, in this embodiment, extends from a distal end of biasing panel 508 to the base of scapula engagement panel 236, and is adjustable using hook and loop fasteners, buckles, or other known means to achieve a desired tension.

Figure 22:
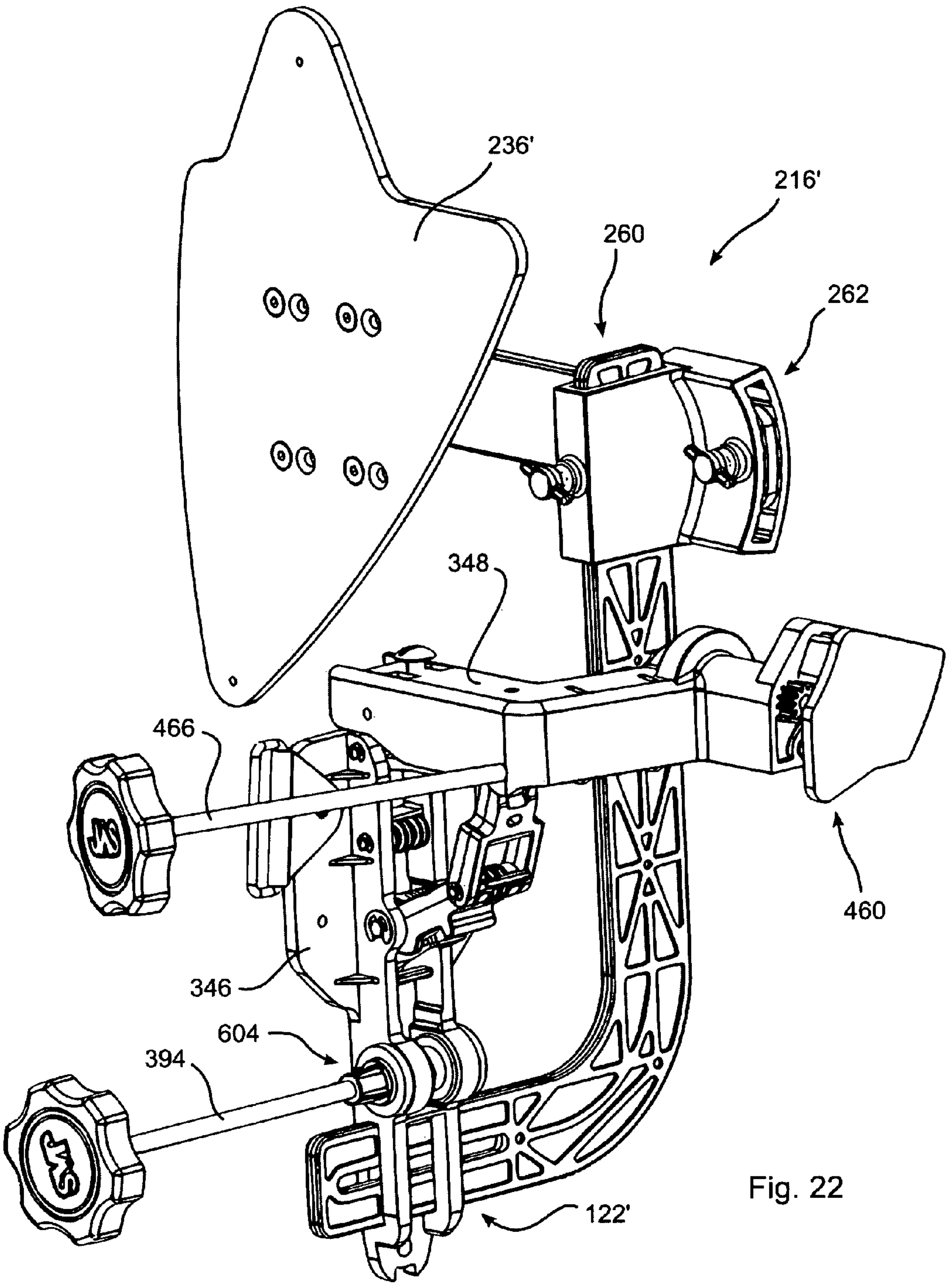
FIG. 22 is an alternative view of the device of FIG. 19, with a limb supporting subsection removed.

An alternative scapula stabilization subsection 216' is illustrated in FIG. 22. Sliding connections 122', 260, and 262 enable accurate positioning of scapula engagement panel 236'. An additional connection 264, visible in FIG. 20, is provided to adjustably connect scapula engagement panel 236'.

Figure 24:
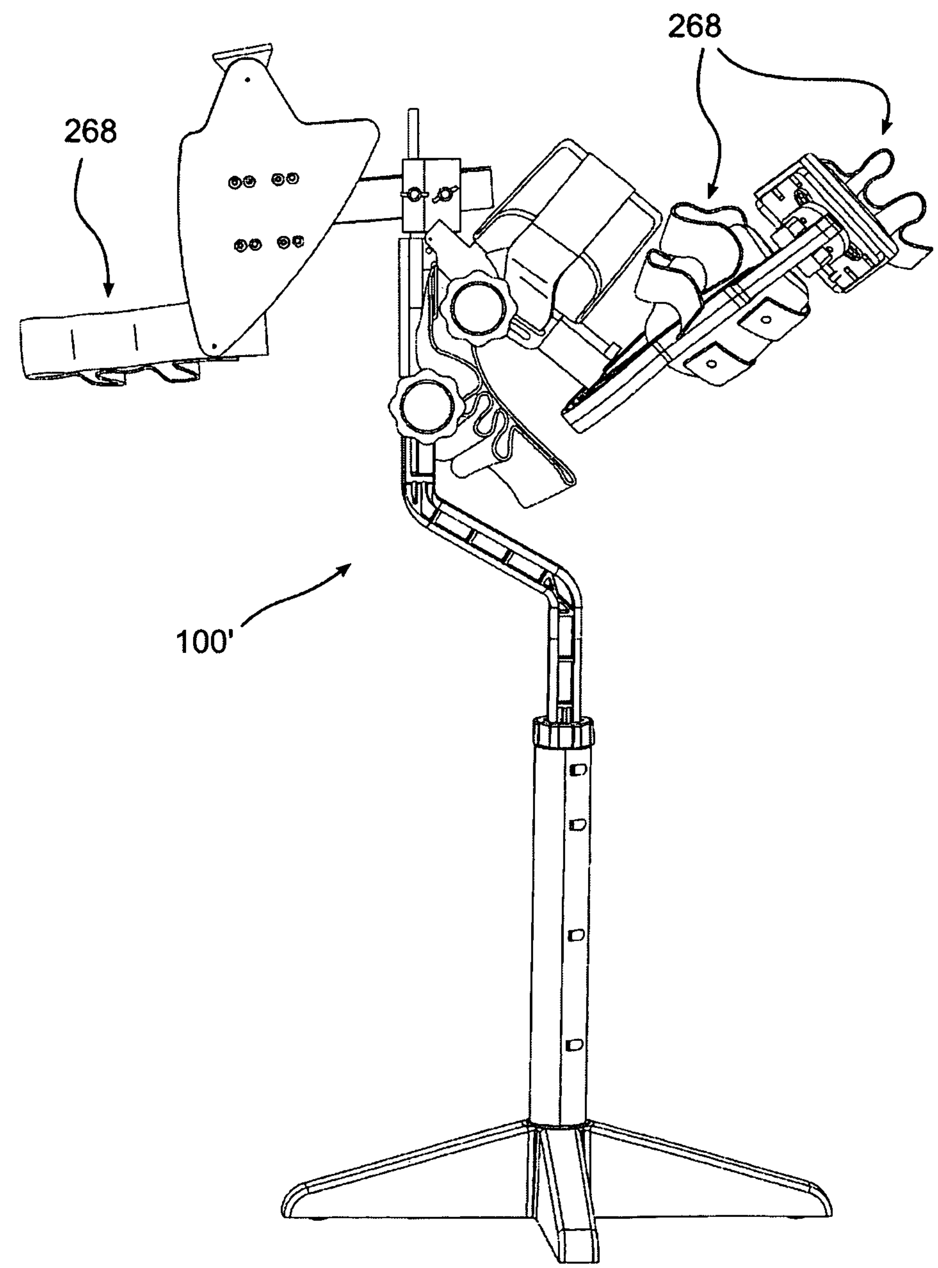
FIG. 24 is an alternative perspective of the device of FIG. 20.
Figure 25:
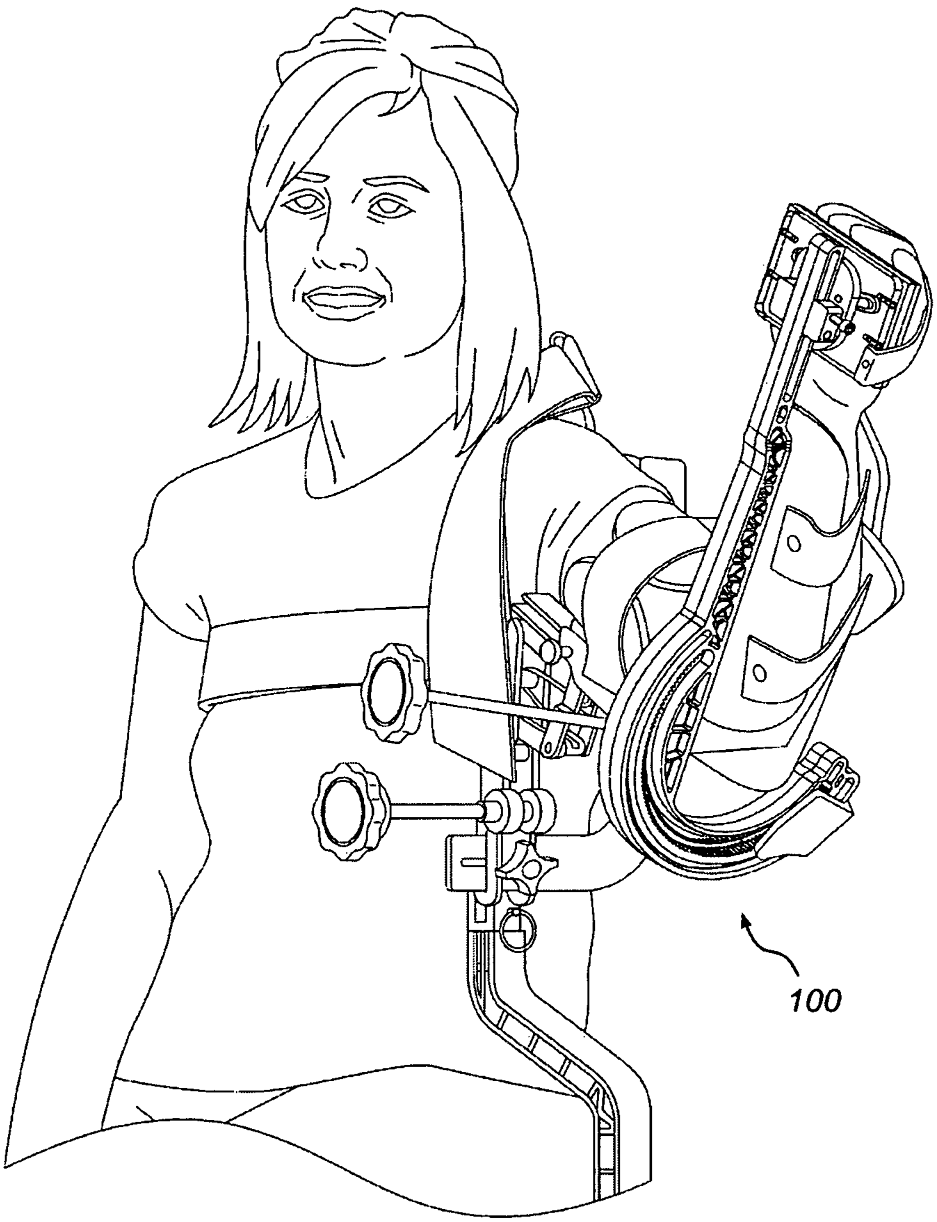
FIG. 25 illustrates a patient undergoing therapy using an orthosis device in accordance with the invention, with the arm positioned at 90 degrees external rotation.
Figure 26:
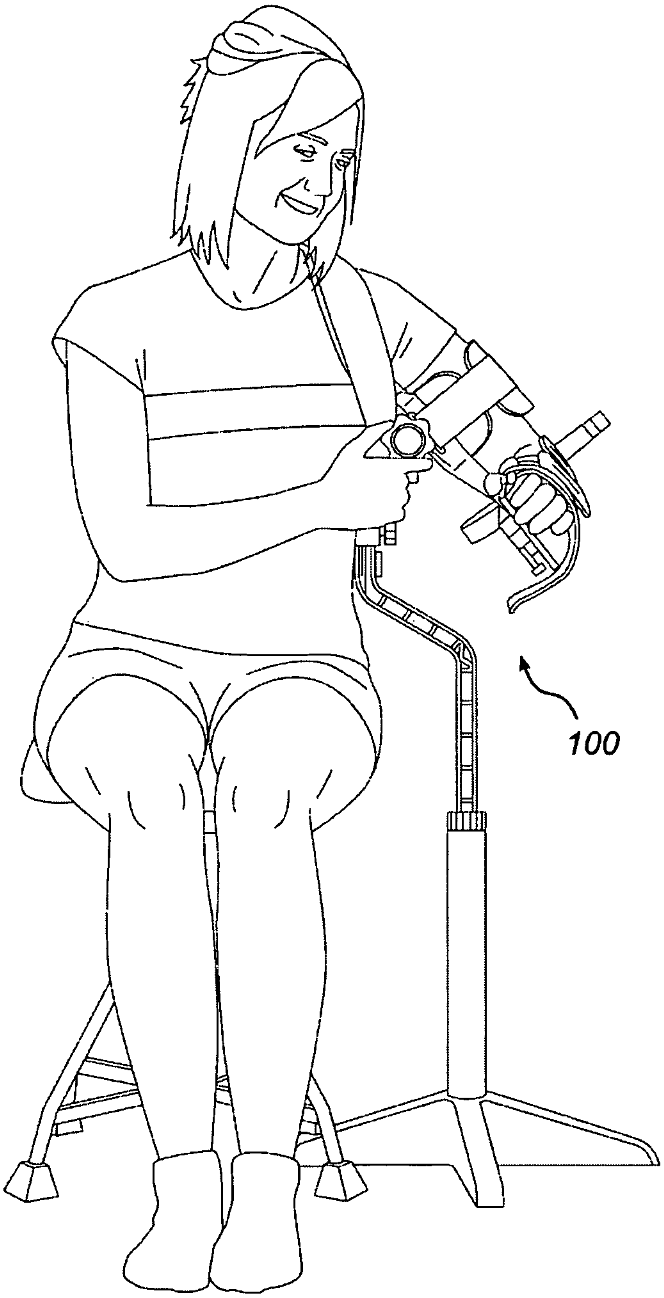
FIG. 26 illustrates the device of FIG. 24, with the shoulder positioned at 25 degrees abduction, where the patient is adjusting a tension of the device.
Figure 27:
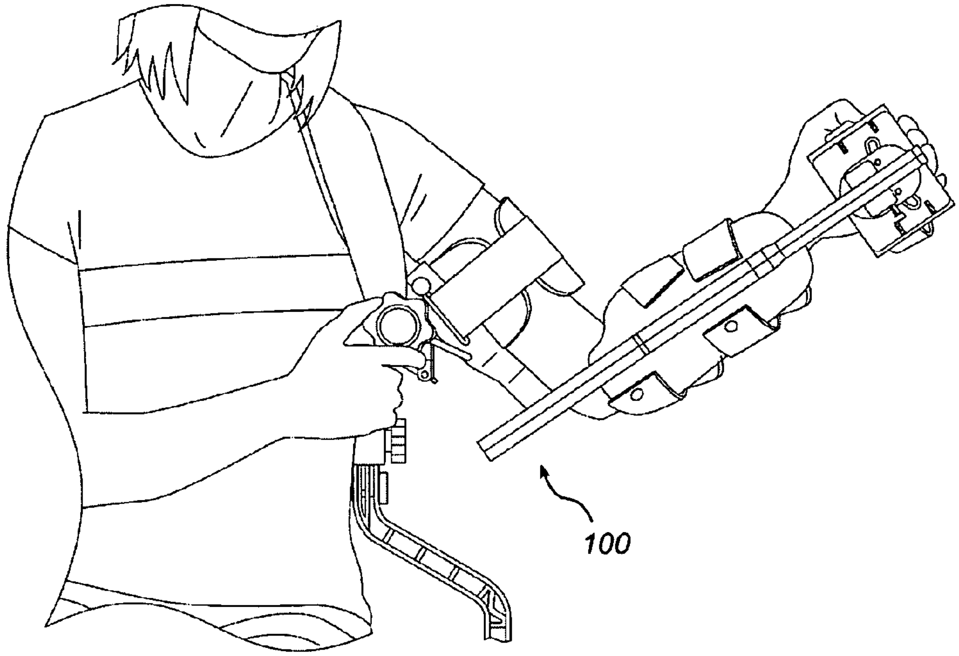
FIG. 27 illustrates the device of FIG. 24, with the shoulder externally rotated and abducted.
Figure 28:
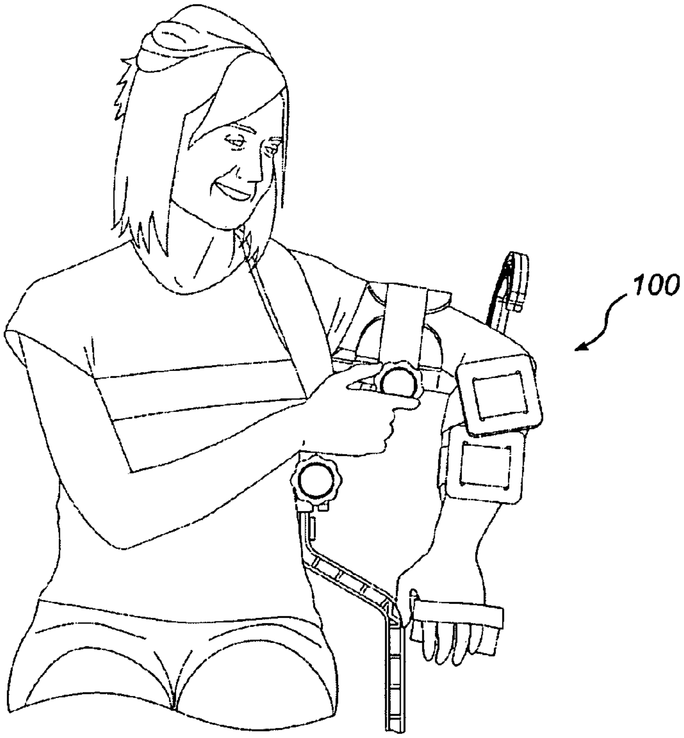
FIG. 28 illustrates the device of FIG. 24, with the shoulder positioned at 90 degrees internal rotation.
Figure 29:
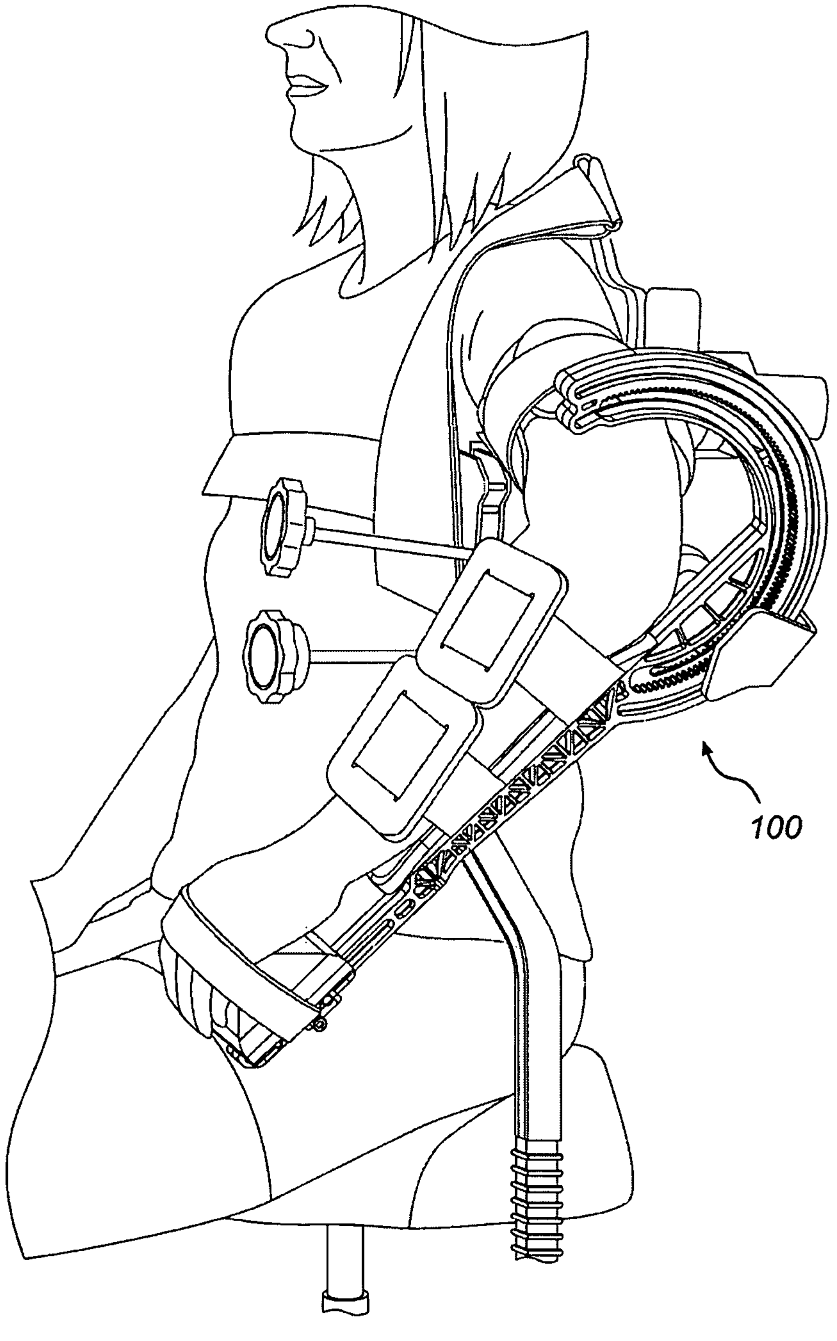
FIG. 29 is a side perspective of the shoulder position of FIG. 28.

FIG. 24 illustrates a device 100' in accordance with the invention, including straps 268 for attaching device 100' to a patient.

Dynamic Tensioning

Figure 7:
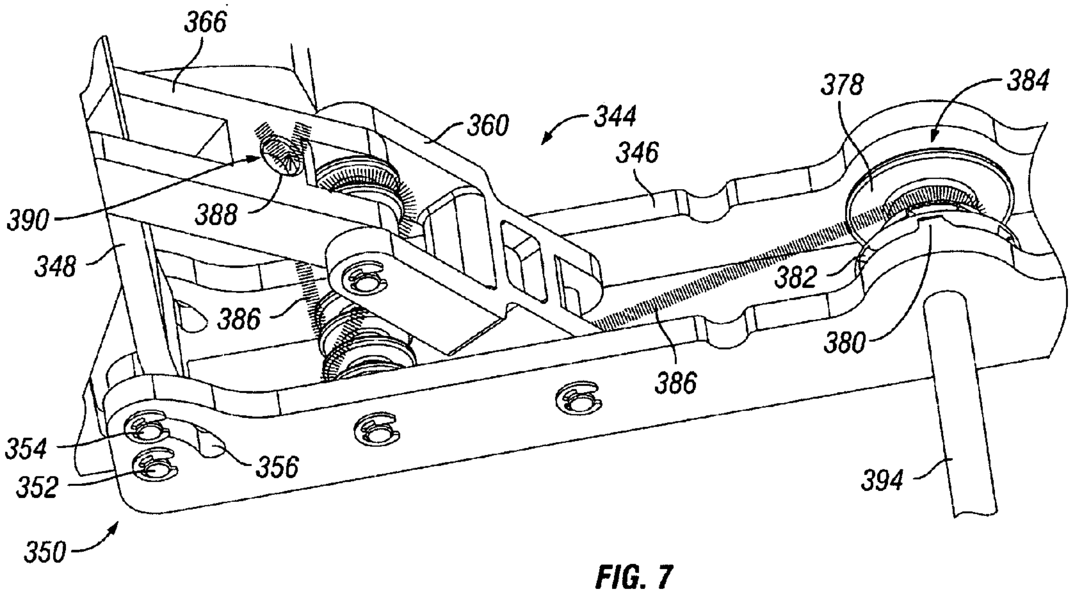
FIG. 7 is a schematic view of a force application assembly in accordance with the invention, illustrating a cable path.
Figure 7A:
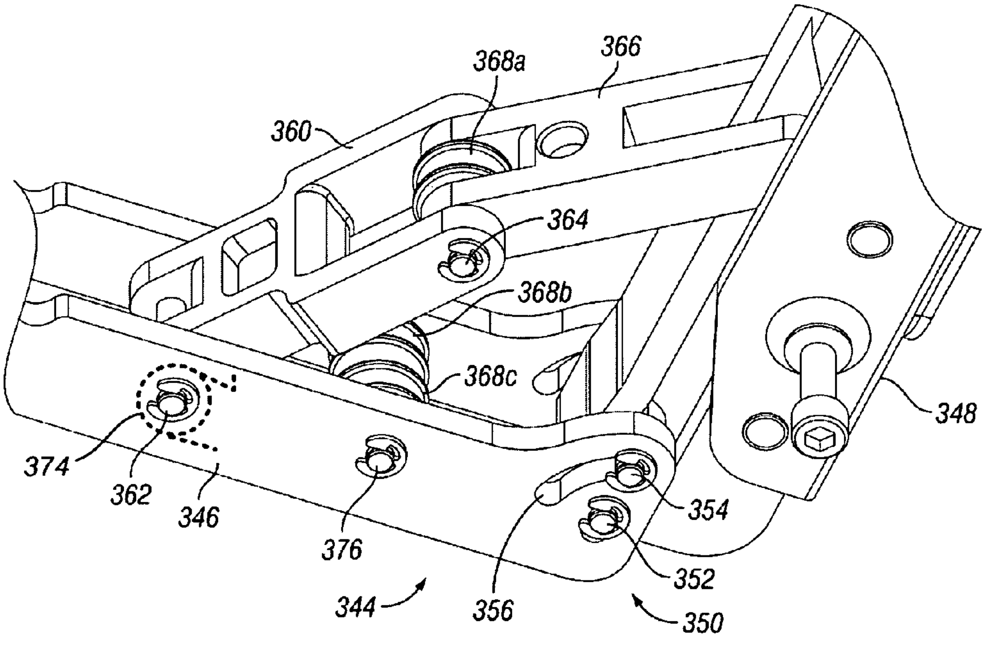
FIG. 7*a* is a detail view of the assembly of FIG. 7, with the cable removed.
Figure 7B:
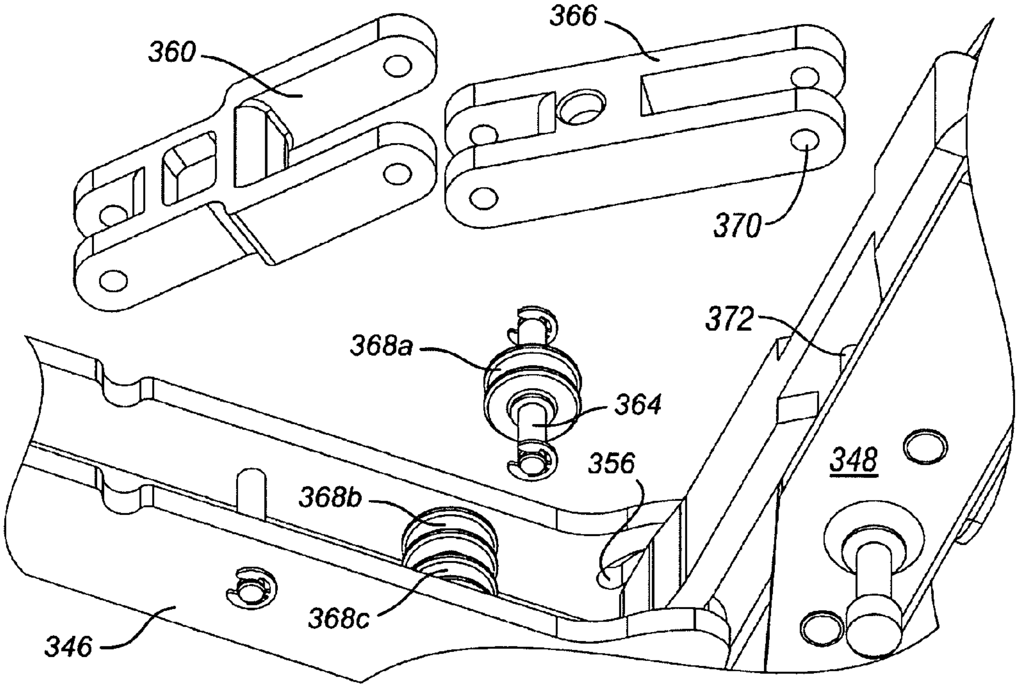
FIG. 7*b* is an exploded view of the assembly of FIG. 7*a;*

Referring now to FIGS. 7-7B, further connected to frame 118 is a hinged force application structure 344, including a proximal frame bracket 346 and distal frame bracket 348, hingedly connected one to the other at hinge 350. In this embodiment frame brackets 346,348 have elongated rectangular forms, although other shapes may be employed. As may be conveniently viewed in FIG. 7, frame brackets 346,348 are connected by pivot pin 352, and are limited in relative angular displacement by pin 354, residing within limiting slot 356. Slot 354 is advantageously sized to permit the maximum range of motion anticipated to be required, while maintaining the hinge within a suitable orientation for ready use.

Force application structure 344 includes means for stretching tissue of the shoulder joint, and provides for dynamic tensioning. In particular, proximal frame bracket 346 supports a proximal shackle 360 pivoting about shackle pin 362. Clevis pin 364 pivotally binds shackle 360 to mating distal shackle 366, and further supports pulley wheel 368*a*. Distal shackle 364 pivotally engages distal frame bracket 348 through connection with pin 372 passing through aperture 370.

Pin 376, passing through proximal frame bracket 346, rotatably supports two pulley wheels 368*b*,368*c*. A resilient cable 386, visible for example in FIG. 7, is partly wound upon spool 378. A one way clutch comprising fixed, ramped pawl teeth 380, and mating slots 382 within spool 378, enable a tensioning rotation in one direction only. Spring 384, visible in FIG. 7, urges spool 378 against pawl teeth 380. To disengage tension, spool 378 is pressed, as with fingertips, away from engagement with pawl teeth 380, compressing spring 384, whereupon spool 378 is free to counter rotate. Spool 378 is rotated by knob 392, connected to spool 378 by shaft 394.

Cable 386 is affixed to, and wraps partially around spool 378, extending thence partly around one of wheel 368*b* or 368*c*, then around wheel 368*a*, then partly around the other of wheel 368*b* or 368*c*, and finally to a tether on distal shackle 366, as in a knot 388 tied in cable 386, on an opposing side of an aperture 390 within distal shackle 366. The manner of affixing cable 386 may be varied as known in the relevant art. The pulley configuration described operates to pull clevis pin 364 towards hinge 350 as spool 378 is wound in a tightening direction. Pulley wheels 368*a,b,c* operate together to increase the mechanical advantage of the force applied to spool 378, facilitating operation by a user. In the embodiment shown, a mechanical advantage is obtained resulting in one third less force required to rotate knob 392. Other pulley configurations may be employed within the scope of the invention, as would be understood by one skilled in the art.

With reference to FIG. 7A, torsional spring 374, disposed about shackle pin 362, is operative to maintain a minimum tension on cable 386, to reduce entanglement, and to maintain cable 386 in proper engagement with wheels 368*a,b,c* when spool 378 is not maintaining cable 386 in a tensioned configuration. Spring 374 urges proximal shackle to pivot in a direction away from hinge 350. Spring 374 may further be selected to apply a therapeutic force, in addition to the resilient force of cable 386.

While a shackle 360 and pin 362 are described in connection with changing an angle of frame brackets 346 and 348, it should be understood that other methods may be employed, as are known in the art or which may be discovered. For example, a cantilever (not shown) may extend from frame bracket 346, acted upon by cable 386 connected at a cantilever extremity.

Cable 386 may be composed of any of a variety of materials, including natural or synthetic fibers, solid, wound or braided materials, or other durable and flexible material selected for a desired resiliency based upon an intended therapeutic application. Examples include cotton or polypropylene cord, plastic tape or strands, wire wound spring or woven wire fabricated from stainless steel or shape metal alloy material, and rubber or latex containing material. Accordingly, the resiliency of the cable may be selected by the type of material, as well as how it is prepared. In accordance with the invention, a cable may be selected to exhibit a significant resistance to stretching, such as a steel cable, or the ability to stretch considerably, such as a rubber or latex cable. The practitioner may thus select a cable resilience to correspond to the therapeutic objective. Additionally, depending on the materials and configuration of device 100 or 100', resiliency may be contributed by the device itself, wherein a cable is selected in consideration of the observed resiliency of the device as configured.

During use, knob 392 is rotated to advantageously produce abduction of the shoulder joint. As knob 392 is rotated, the angle between proximal and distal support members increases, increasing an angle of frame brackets 346 and 348, stretching tissue associated with the joint. During static stretching, as tissue stretches, the force required to maintain a stretched position decreases, and may ultimately fall to zero. If cable 386 is resilient, however, a minimum amount of dynamic stretching force is maintained throughout the stretching period. The amount of dynamic stretching force is a function of the resiliency of cable 386.

Figure 15:
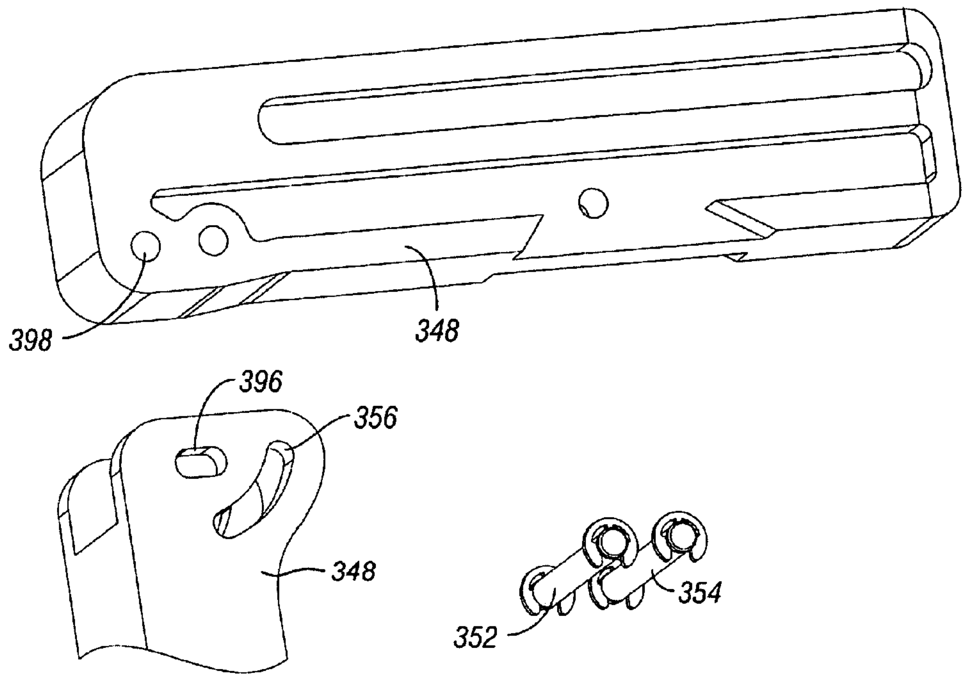
FIG. 15 is an exploded view of a hinged portion of the force application assembly of the device of FIG. 1.
Figure 16:
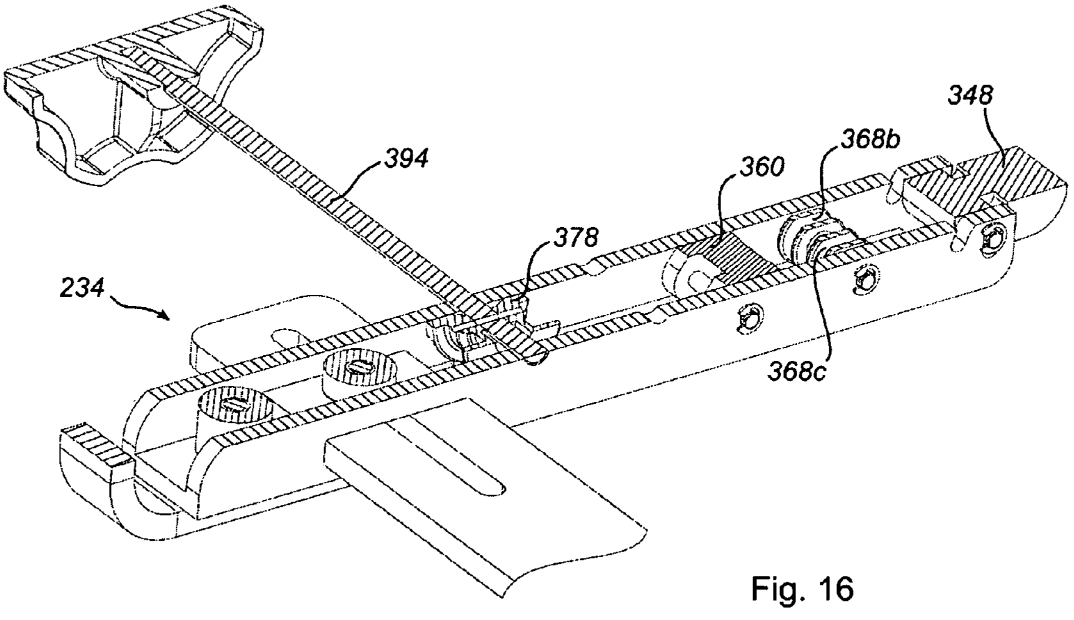
FIG. 16 is a section of the force application assembly of the device of FIG. 1.
Figure 17:
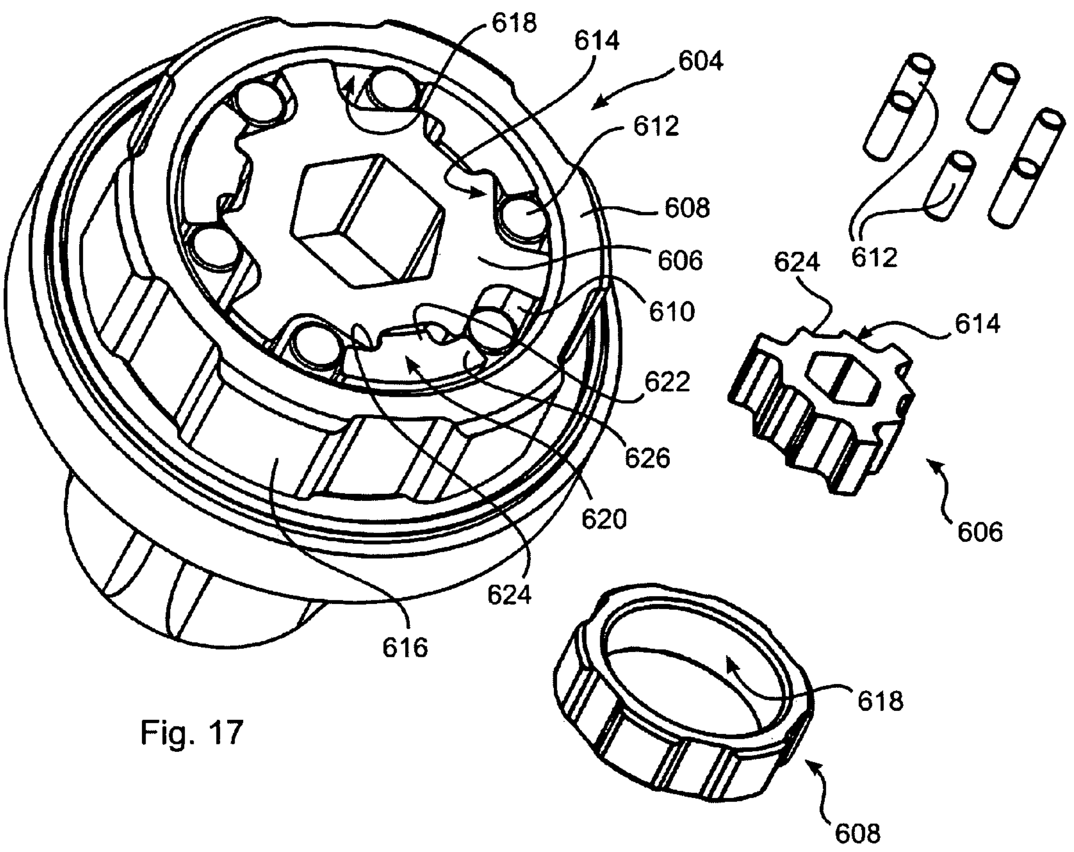
FIG. 17 is a perspective view of a rotation control device of the invention.
Figure 18:
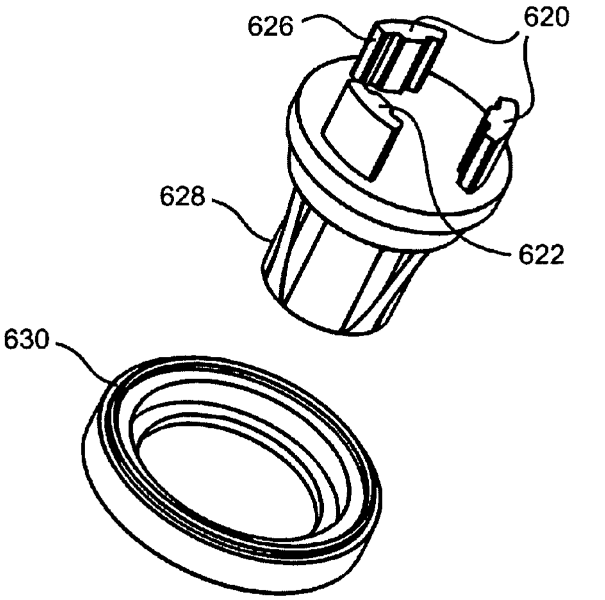
FIG. 18 is an exploded perspective view of the rotation control device of FIG. 17.

With reference to FIG. 15, slot 396 and hole 398 house pin 352, together forming a pivot between proximal and distal frame brackets 346,348. Slot 396 is elongated, and slot 356 is configured with in increasing radius. Accordingly, as the angle between frame brackets 346,348 increases, distal frame bracket 348 is caused to move further from the body of the patient. This outwards movement with respect to the body causes a distraction of the shoulder joint, further stretching the tissue of same. The extent of distraction can be varied or eliminated based on the radius of slot 356, and commensurate length of slot 396.

It should further be understood that force application structure 344 may sized and configured to stretch tissues of other joints.

Rotation Control

With reference to FIGS. 17-20, in accordance with the invention, the drive assembly 600 includes a drive shaft 394, rotated by hand or an actuator such as a motor 634, to set a position of the device 100. Motor 634 may further be controlled by servo control circuits 636, the circuit possibly including a computer with a human interface 640 connected by wires 638, or a wireless network 642. Static or dynamic tensioning is achieved by rotating drive shaft 394, which operates to impart a force to device 100, for the therapeutic benefit of the patient.

A rotational position of drive shaft 394 is maintained by a rotation control device 604, which enables an operator to rotate the drive shaft to adjust a tension of the device, and concomitantly prevents rotation of drive shaft 394 incident to forces imparted by a load. Loading forces include, for example, gravitational forces acting upon the body, or body tissue resisting stretching.

The rotation control subassembly 604 includes inner and outer raceways, or races 606,608 respectively, defining a space 610 therebetween, and rotatable elements, such as pins 612 or spheres, disposed within space 610. When one of race 606,608 is rotated with respect to the other, pins 612 are urged along a ramp 614 associated with one of the races 606,608, whereby pins 614 become pinched and bind between ramp 614 and an inner surface 618 of outer race 608, thereby preventing further movement, or creating a lock-up condition, of one race relative to another. Ramps 614 are provided for both possible directions of rotation of race 606. One race 608 is fixed against rotation, whereby when the raceways become fixed relative to each other, neither raceway rotates with respect to the device. Projections 616 in race 608 are provided to engage matching shapes (not shown) in a frame member in which race 608 is mounted, for example proximal frame bracket 346. In this manner, race 608 cannot rotate relative to device 100, or drive assembly 600.

Drive shaft 394 is connected via bushing 628, or other known means, to a series of engagement dogs 620, which are interposed in space 610 between the inner and outer races 606,608. When drive shaft 394 is rotated, bosses 622 associated with dogs 620 engage cams 624 associated with race 606, whereby drive shaft 394 operates to rotate, or drive, race 606. Engagement dogs 620 simultaneously impinge at surface 626 upon pins 612, enabling free rotation of drive shaft 394 by ensuring that pins 612 do not travel sufficiently far along ramp 614 to bind between races 606,608.

A lever, associated with the driven raceway 606, is operated when drive shaft 394 is rotated, and causes a tensioning member to tighten or loosen as drive knob 392 is rotated. In one embodiment, the lever is a spool 378, and the tensioning member is a cable 386. Any form of cable or cord, spring, or other force transferring device as described herein may be used with the rotation control device 604. While a spool is shown connected to rotation control device 604, it should be understood that other devices operative to transfer the rotational force to cable 386 may be used, including a bar, eccentric spool or cam, pincher, or grasper. In each case, the rotational force imparted by drive shaft 394 is applied to the other device to cause the device to apply a tensioning force to cable 386.

In the embodiment illustrated, inner race bears ramps 614, however it should be understood that one skilled in the art could switch the roles of the inner and outer ramps, whereby ramps 614 are disposed upon an inner surface of an outer race, and the inner race is fixed.

A retainer 630, and other supporting means, may be provided to secure the components of rotation control subassembly 604 together. Additional components may be included, as known by one skilled in the art, to secure subassembly 604 within drive assembly 600. A shaft, not shown, engaged within shaped aperture 632, connects to spool 378.

While rotation control device 604 is illustrated in the context of a tissue stretching device, herein, it should be understood that the device may be used in conjunction with any device for which it is desired to prevent rotation due to a load, and enable rotation due to a driven input. Other examples include tissue manipulation or stretching devices for other joints, implantable devices for which rotation must be controlled, and external devices, including mono-lateral and Ilizarov external fixateurs.

Rotation control device 604 may be formed to stop rotation in only one direction, if desired. For example, pins 612 may be removed for one direction of rotation. Alternatively, other modifications may be made as would be understood by one skilled in the art, for example, removal of cams 624 in one direction, or modification of the shape of dogs 620 in one direction.

Static Tensioning

Referring again to FIG. 4, distal frame bracket 346 may be seen to extend away from hinge 350, and to support a gear driven force application structure 458. Elements of structure 458 are described in detail in U.S. patent application Ser. No. 11/533,839, and U.S. Pat. No. 7,112,179, as previously incorporated by reference herein, above. Reference may be had to the cited references for such detailed description; however the structure will be further described herein, in the context of the entirety of device 10, and to detail improvements and further advantages appurtenant thereto.

Figure 8:
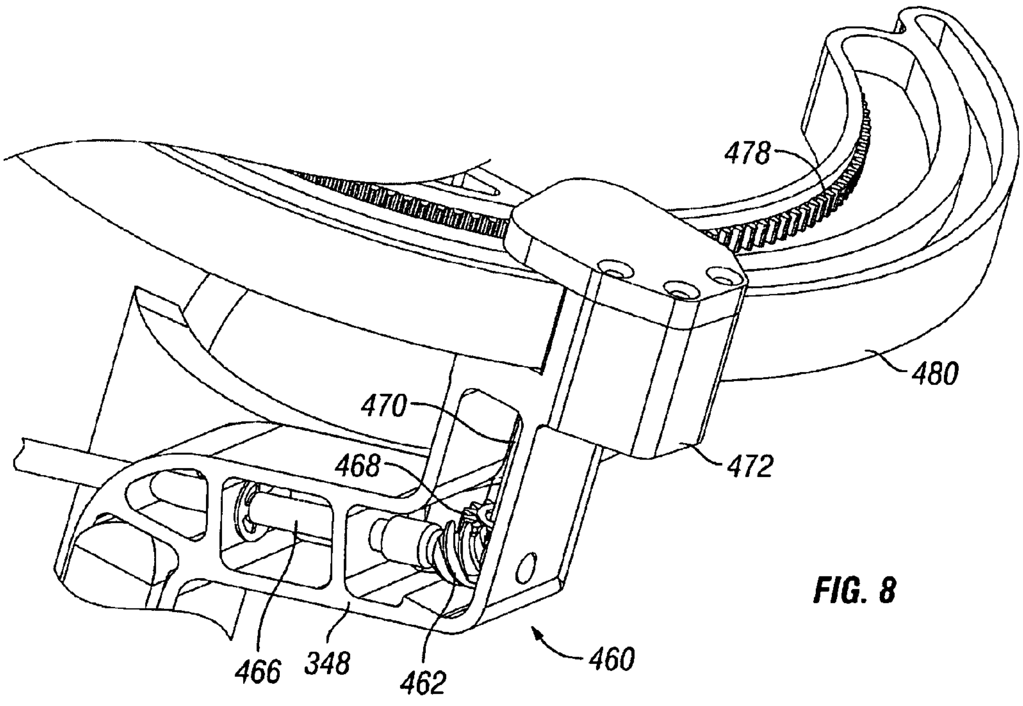
FIG. 8 is a detail of another force application assembly in accordance with the invention, illustrating gears.

In particular, with reference to FIG. 8, a distal support member gear housing 460 is provided within distal frame bracket 348, supporting a first gear 462 connected to a gear angle adjusting knob 464 via shaft 466. Mating second gear 468 engages first gear 462, and through their mutual engagement, permits the angular translation of rotational movement of adjusting knob 464. As such, adjusting knob 464 may be positioned in a location convenient for the wearer or practitioner to perform adjustments, as described in the cited references, and elsewhere herein. In the embodiment shown, first gear 462 is a worm gear, and second gear 468 is a spur gear, although it should be understood that the angular translation may be accomplished through other means. In particular, in accordance with the invention, gears 462 could be a worm, and 468 a worm gear, thereby providing the advantage of resistance to reversal, and further facilitating implementation of a gear reduction, operative to ease adjustment of force application structure 458.

Figure 9:
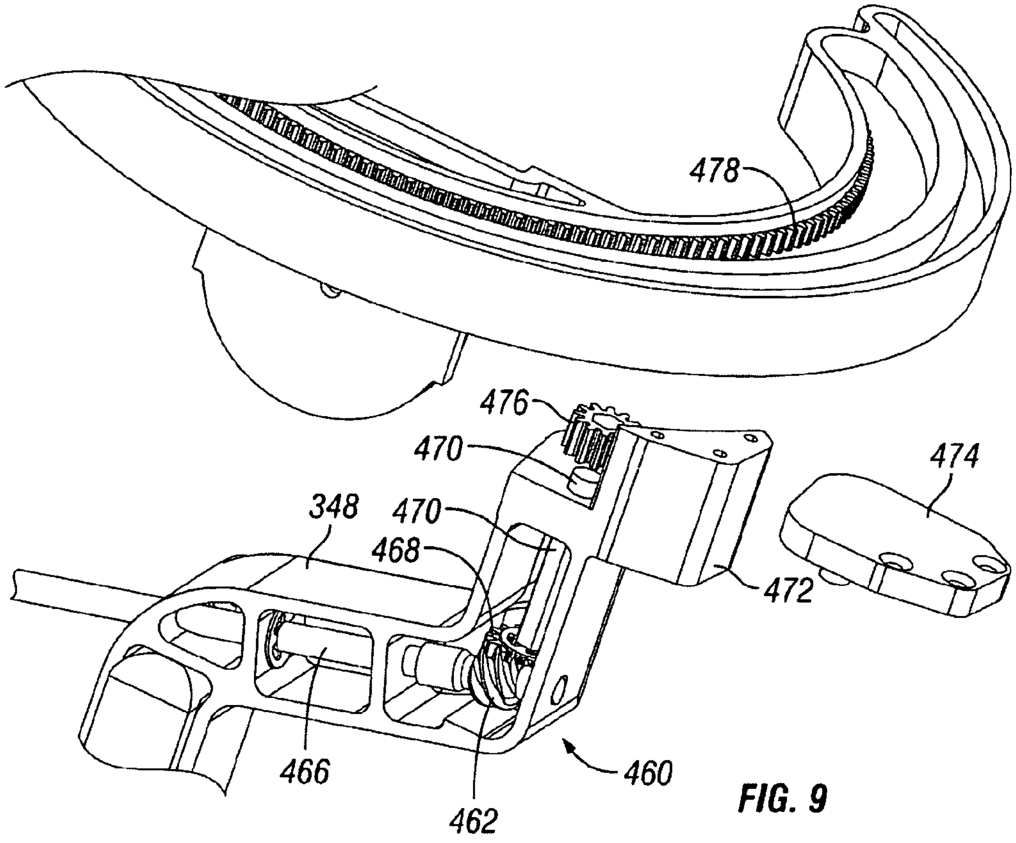
FIG. 9 is an exploded view of the assembly of FIG. 8.

A shaft 470 connected to gear 468 extends into arcuate connector support housing 472. The interior of arcuate connector support housing 472 may be seen in FIG. 9, wherein housing cover 474 is moved aside, revealing internal arc driving gear 476 connected to shaft 470. Arc driving gear 476 drives a rack gear 478 disposed within arcuate support 480. As adjusting knob 464 is rotated, the rotational movement is translated through gears 462,468 to turn shaft 470, thereby turning gear 476, driving rack gear 478, whereupon arcuate support 480 is caused to move through arcuate connector support housing 472.

A limb support member 500 is provided, connected to arcuate support 480, operative to support a limb or jointed body part. In the embodiment shown, support member 500 is sized and shaped to fit the forearm and hand of a device user, and includes a forearm support 502 and hand support 504. As shown in FIG. 13, a forearm strap 516 and hand strap 514 provide further support and fixation, the forearm strap, in particular, preventing the elbow from lifting out of position as a therapeutic force is applied. Limb support member 500 is oriented and arranged in connection with arcuate support 480 so that a limb may be secured therein, and as arcuate support 480 is moved by rotation of gears 462,468,476, the joint is flexed or extended along a natural physiological path. Upper arm cuff 506 is connected to distal frame bracket 348, operative to maintain an upper limb in correct orientation with respect to positioning a joint in alignment with arcuate support 480, as described.

Figure 14:
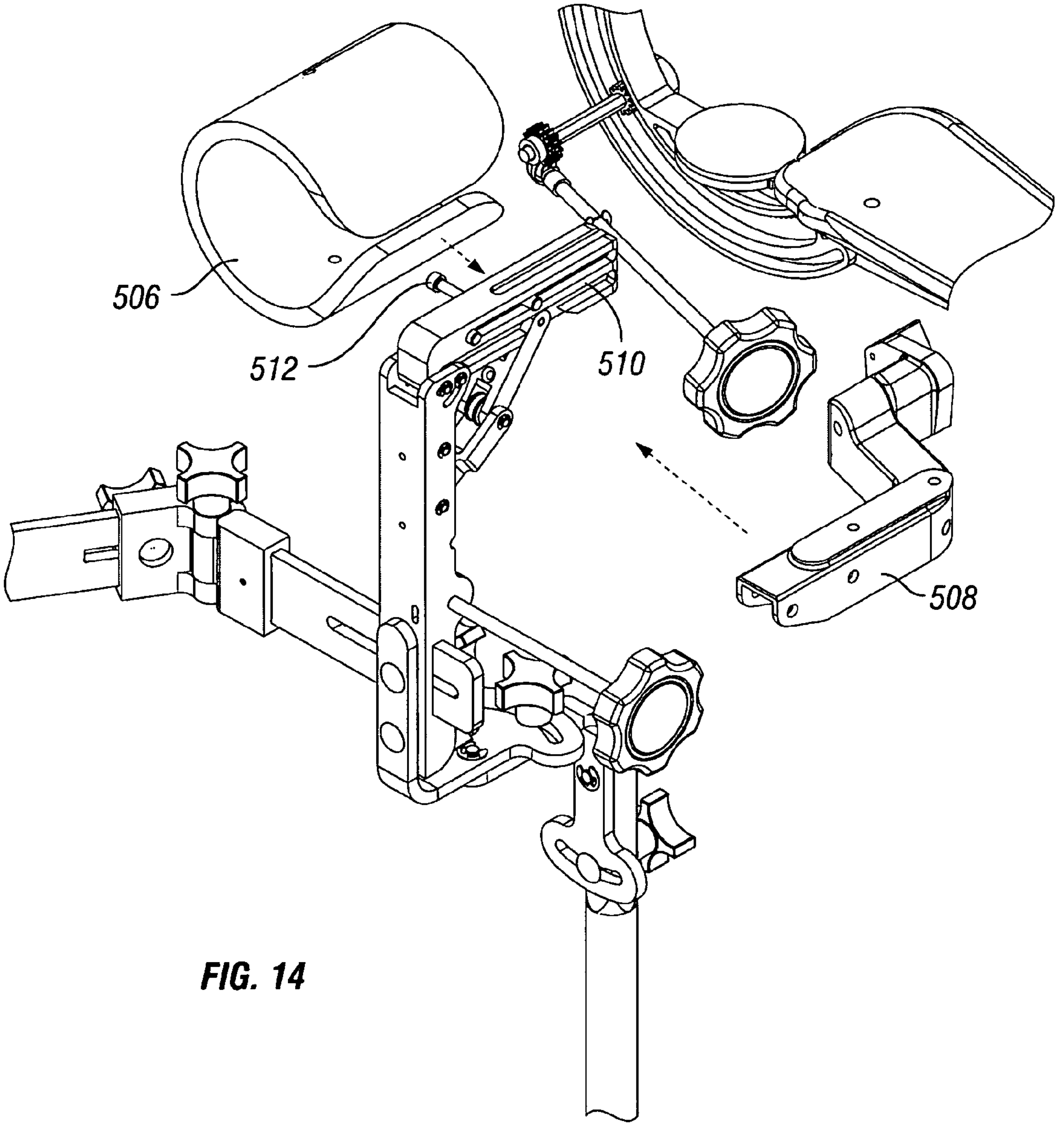
FIG. 14 is an exploded view of the device of FIG. 1, illustrating a cuff adjustment mechanism in accordance with the invention.

Cuff 506, forearm support 480, and hand support 504 are adjustable to fit arms of varying proportions, as described in the cited references, and as described further herein. In particular, with reference to FIG. 4, adjustment 508 enables movement of hand support 504 towards or away from the axis of rotation of arcuate support 480, allowing for varying forearm lengths. Adjustment at 238 places the scapula engagement panel 236 in correct alignment. Further, with reference to an exploded view in FIG. 14, cuff 506 is connected to cuff support 508, the latter slidably supported within cuff support retainer 510, to adjust for the patient's arm length. When cuff 506 is positioned in a desired location, adjusting knob 512 is tightened.

In use, as knob 464 is rotated, internal or external (medial or lateral) rotation is effectuated. Gears 462,468 maintain a set angular position, although other means known in the art may be employed to prevent unwanted rotation of gears 462, 468 after attaining a desired position. When a patient is properly positioned within device 100, the pivot point of internal/external rotation is along the axis of the upper arm.

When stretching tissue of the shoulder, internal/external rotation angle is set for optimized beneficial effect with respect to the glenohumeral joint. During the course of therapy, the internal/external rotation angle may be changed to alter to application of force at the glenohumeral joint. Moreover, as explained in detail in the cited references, the internal/external rotation angle may be changed to effectuate a therapeutic benefit upon the elbow. It should further be understood that effectuators as are known and described in the art may be fitted to the wrist portion of device 100 in order to carry out stretching therapy upon the wrist.

Operating Range

The following joint movement ranges have been found to be advantageous:

| Motion | Degrees |
|---|---|
| Shoulder Flexion | 60 |
| Shoulder Extension | 30 |
| Internal Rotation | 90 |
| External Rotation | 90 |
| Min Abduction | 25 |
| Max Abduction | 90 |

The preceding ranges are reflected in the design of the illustrated embodiment. It should be understood, however, that should a health practitioner deem it desirable, device 100 may be adapted for wider ranges without departing from the spirit and scope of the invention. Such adaptation may be accomplished by changing the relative dimensions of the various described elements, as would be understood by one skilled in the relevant art.

Devices in accordance with the invention can be made using flexible or rigid polymeric material, metal, or other biocompatible materials capable of exerting loading when flexed, stretched or compressed. An exemplary orthosis, including a flexible section is disclosed in U.S. Pat. No. 5,685,830 entitled "Adjustable Orthosis having one-piece connector section for flexing" to Bonutti, the contents of which are herein expressly incorporated by reference in their entirety.

For portability, ease of setup, reduction of cost, ease of cleaning, and durability, devices in accordance with the invention are advantageously fabricated from light weight aluminum and plastic. For transport or storage, feet 132 are folded against base member 128. Stabilization subsection may be removed at sliding engagement member 234. Further, limb engaging portion 114 may be removed at adjustable connection 120. Additionally, hinge 350 may be collapsed for a reduced profile.

Flexible sections can be made of a shape memory or reactive material, where a change in temperature, or application of an electrical current, results in a shape or position change of the flexible section. The change in shape of a flexible section can be used to change the position of adjacent frame brackets. Alternatively, the change in shape of a flexible section can be used to provide a force to adjacent frame brackets.

In an exemplary use, the device or orthosis 100 is operated to extend a joint in the following manner. Knob 392 is rotated to cause connective tissue of the joint to be stretched, as described. The orthosis 100 is maintained in a position for a predetermined treatment time, utilizing the principles of stress relaxation to stretch the connective tissue of the joint. As explained above, prior art orthoses may allow the tissue to partially relax as the tissue stretches because the devices simply held the body members in a fixed position. The invention may further utilize a resilient force, for example where a resilient form of cable 386 is used, to apply loading or forces to the joint. This application of force prevents a relaxation of the connective tissue of the joint, utilizing the principles of creep to further stretch the connective tissue of the joint. After the expiration of the treatment time, the orthosis 100 may be returned to an initial position, relieving the joint. While in one embodiment, the loading or forces applied are substantially constant, they also may gradually increase, decrease, pulse between a first and second amount of force, or be varied in other ways such as described in the cited references.

Optionally, knob 392 can be rotated to a third position, further increasing the stretch of the connective tissue of the joint, for example at discrete time intervals to incrementally increase the stretch of the joint through the treatment cycle. In each of the movements, cable 386 provides a substantially constant force to the joint, preventing a relaxation of the connective tissue of the joint. After completion of the treatment cycle, the knob may be counter rotated, and spool 378 may be moved away from engaging pawls, as described above, to relieving tension on the joint The force applied in one treatment interval may differ in degree, profile, or duration of force applied in another treatment interval, although in some cases the applied force may be substantially the same for two or more, or even for all treatment intervals.

The degree of force applied, for example, may be varied from one treatment interval to another, and likewise the degree of force applied may be adjusted depending upon different factors or patient needs.

Additionally, adjustments also may be made during a treatment interval. For example, adjustments may be made during a treatment interval in order to increase or decrease the forces imparted, even though the geometric angle or position of the device remains unchanged. In one example, the initial force imparted at the beginning of a treatment interval may be low, but then increased over time according to a patient's progress or according to a predetermined time schedule. In another example, it may be desirable to initially apply a greater force in order to help accelerate a patient's progress, but then later relieve or reduce the forces applied after achieving a satisfactory degree of stretching or after a predetermined time.

In addition, the force application structure 344 can include a force control system for control of the force applied, as in an automated control for rotation of knob 392 or shaft 394. A pneumatic or hydraulic system, for example, may have controls for the amount of force imparted by any or all of the force elements as well as the force profile and direction of applied forces. Likewise, a servo-mechanical force control system may be used to vary the amount of deflection or preload of spring-like force elements. These auxiliary systems could be under control of a computer. The computer could control joint stretching based upon sensors, including sensing of physiological indicators.

Moreover, while the examples and descriptions provided herein illustrate how the invention may be used to treat flexion and extension contractures, the concepts may also be applied to treating contractures limiting rotational range of motion. Thus, the devices described herein also may be configured to increase the rotational range of motion, such as supination or pronation, for a joint in addition to, or instead of, treating bending. For example, a device for treating contractures in a shoulder, elbow, wrist, hip or ankle joint may be configured to help enhance rotational capability of the joint.

It should be noted that the term "cuff" as used herein means any suitable structure for transmitting the force of the orthosis to the limb portion it engages. The cuffs, e.g. 502,506 can include a strap, such as hook and loop strap, and foam portions to secure the cuffs to the body portions.

In an embodiment in accordance with the invention, an electric motor (not shown) is mounted to shaft 394, and or shaft 466. A battery (not shown) may provide electric power to the motor, or it may be powered from another source. A microprocessor (not shown) can be used to operate the motor to more accurately control positioning of the frame brackets, or to allow for automation of some steps of treatment such as moving from one position to another. The motor may also operate within a control system that allows for remote operation of the device by a healthcare professional or technician. The microprocessor and motor together can be used to cycle the proximal and distal frame brackets 346,348 through abduction or adduction a certain amount, hold a position while tissue stretches, then move further in that direction; or in any other manner. In another manner of use, the orthosis can be set to cycle to one end of the joint's range of motion and hold there for a predetermined period of time, then cycle to the other end of the joint's range of motion and hold there. Given the benefit of this disclosure, skilled artisans would understand how to program and control the microprocessor so that desired motion is attained. This embodiment is ideally suited for continuous passive motion exercise, because it can be programmed with the desired sequence of movements. Preferably, at least this embodiment of the invention also would be a portable device so that it may be provided to a patient to use in the home, at work, or wherever they may desire.

It should be understood that the particular physical arrangement of the motor, the battery, and the microprocessor may be varied, as known in the relevant art. Additionally, another type of actuation, other than an electric motor, can also be used. For example, the use of a hydraulic or pneumatic motor as the drive mechanism is contemplated.

The invention can further include a monitor for use with device 100, which provides assurances the patient is properly using device 100 during his/her exercise period. For instance, the monitor can have a position sensor, a temperature sensor, a clock or timer, or a device type sensor for monitoring the patient's implementation of a protocol. The information obtained from these monitoring devices may be stored for later analysis or confirmation of proper use or may be transmitted in real-time during use of the device. The data obtained from the monitor can be analyzed by a healthcare professional or technician and the protocol can be adjusted accordingly. This analysis may be conducted remotely, thereby saving the time and expense of a home visit by a healthcare professional or technician. An exemplary monitoring system is provided in U.S. Publication No. 2004/0215111 entitled "Patient Monitoring Apparatus and Method for Orthosis and Other Devices," to Bonutti et al., the content of which is herein expressly incorporated by reference in its entirety It should be understood that the orthosis of the invention can be used to extend, flex, or rotate other joints in the body, such as an ankle, knee, finger, wrist, or elbow joint, with the construction of the orthosis in such case being varied to fit the particular application. The orthosis can be used, for example, to flex the ankle joint to stretch a tight achilles tendon in cerebral palsy or post traumatic contractures. It may also be especially useful in obtaining the last degrees of joint extension. The orthosis can be custom made to fit a particular individual, or can be an off the shelf item. The orthosis can also be used, for example, to eliminate contractures or stress soft tissue. It can be used for patients with cerebral palsy, stroke, spastic paralysis, burns, as well as in post-traumatic or post-surgical cases. It can also be used, for example, in therapy after a knee replacement, in which the extremes of motion in extension or flexion are difficult to obtain without extensive intervention of a therapist. As previously discussed, the invention also may be used to extend the rotational capability of a joint.

Additionally, as noted above, the device can be used for tissue transport, bone lengthening, stretching skin or tissue fascia, etc. For example, device of the invention can be incorporated in an external bone fixation device, such as an Ilizarov device, where the device is affixed to the bones on the body portions using pins. The drive assembly 600 and force application assembly 602 can be used for bone lengthening and stretch the surround soft tissue.

Furthermore, the invention is disclosed as utilizing the principle of stress relaxation, and in some instances, creep. However, it is contemplated that the invention can include additional treatment protocols. For example, in continuous passive motion ("CPM"), the device continually moves the joint through a range of motion. The motion may be provided by an electric or hydraulic motor or a pneumatic system attached to the device. As the CPM moves the joint through its range of motion, however, it does not increase the range of motion.

The invention can be incorporated into a CPM device, where the CPM device would stop at an end range position. As previously discussed, a drive assembly 600 may be provided to move the joint from its normal position at the end range position of the CPM to a second position, thereby stretching the tissue using the principles of stress relaxation. As the tissue relaxes, a force application assembly 602 may be utilized to provide an additional force, utilizing the principles of creep to stretch the tissue. After a set time period, the drive assembly 600 may be moved to a third position to further stretch the tissue or the CPM device may resume movement of the joint through the range of motion. Before CPM movement resumes, the drive assembly 600 may be returned to an original position so that the range of motion of the CPM is returned to its original state, or the drive assembly 600 may be used to alter the range of motion that the CPM follows. In this manner CPM device can be utilized to increase the range of motion of the joint.

The components of the invention are rigid members made of, for example, aluminum, stainless steel, polymeric, or composite materials. The member and extensions are sufficiently rigid so as to be able to transmit the necessary forces, and cooperate to provide a resilient force, where dynamic tension is desired. It should be understood that any material of optimal rigidity can be used. More particularly, a resilient frame may advantageously be employed to contribute a continuous force to the joint, cooperating with a resilient cable, or providing the sole resilient force for stretching tissue associated with a joint.

For example, the components can be made by injection molding. Generally for injection molding, tool and die metal molds of the components are prepared. Hot, melted plastic material is injected into the molds. The plastic is allowed to cool, forming components. The components are removed from the molds and assembled. In addition to being bolted together, portions of the device in accordance with the invention may be assembled by welding, adhesives, or other means as known in the art. In addition, adjustable connections may be achieved by clamps, springs, hook and loop fasteners, and other removable means as known in the art.

Furthermore, it is contemplated that the components can be made of polymeric or composite materials such that the device can be disposable. For example, at least some or all of the components can be made of a biodegradable material such as a biodegradable polymer. Among the important properties of these polymers are their tendency to depolymerize relatively easily and their ability to form environmentally benign byproducts when degraded or depolymerized. One such biodegradable material is poly (hydroxyacids) ("PHA's") such as polyactic acid ("PLA") and polyglycolic acid ("PGA").

Additionally, the device can be made of a nonmagnetic material. In such instance, the device can be used as a positioning device for use in imaging devices, such as a MRI device. It is also contemplated that the device can be used as a positioning device for use during surgical procedures, where it may be necessary to adjust and hold the position of the joint.

It should be understood that the static and dynamic portions of the invention as shown and described herein may both be statically adjustable, or both be dynamically adjustable, as defined herein.

All references cited herein are expressly incorporated by reference in their entirety.

It will be appreciated by persons skilled in the art that the invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention.

What is claimed is:

1. A device for stretching tissue of a joint in a body of a patient, said device comprising:

a force application assembly comprising:

a first hinge including a first hinge portion affixable to a first portion of the patient's body on a first side of the joint;

a second hinge portion pivotally connected to said first hinge portion, affixable to a second portion of the patient's body on a second side of the joint; and a spool;

a second hinge connected to said first hinge, operative to increase an angle of the first hinge thereby changing an angle of the joint to stretch tissue of the joint, when an angle of the second hinge is increased;

a first pulley;

a second pulley formed between said first hinge and said second hinge;

a resilient cable operatively engaged with said spool, said first pulley, and said second pulley, wherein said spool is configured to apply a tension to said cable whereby tension on said cable applies a force to said first and second hinges in a direction of increasing an angle of said first and second hinges;

wherein when said free end of said cable is affixed relative to said second pulley, said resilience of said cable is operative to impart a continuous force to said first and second hinges in a direction of increasing an angle of said first and second hinges; and a drive assembly coupled to the force application assembly, said drive assembly configured to move the second body portion with respect to the first body portion, wherein said drive assembly is further configured to maintain said spool in a position of applying tension to said cable; wherein said drive assembly further comprises:

a first circular raceway;

at least one rotatable element;

a second raceway disposed in concentrically rotating conformity with said first circular raceway, having at least one curved surface operative to support said rotatable element between said first and second raceways, whereby when said first circular raceway is rotated in a first direction, said curved surface urges said rotatable element to a position in binding conformity between said first and second raceways, preventing rotation of said first raceway with respect to said second raceway; and a plurality of pins configured to prevent said rotatable element from moving to said position in binding conformity when said second raceway is rotated.

2. The device of claim 1, further comprising:

a gear, connected to said second hinge portion;

a curved rack, driven by said gear;

a frame, connected to said rack, operative to support a third portion of the patient's body; and a shaft configured to turn said gear;

whereby when said gear is turned, said third portion of the patient's body is moved relative to said second portion of the patient's body.

3. The device of claim 1, wherein said first hinge further comprises pivot connection including a slot and a hole, said pivot connection configured to apply a distractive force to the joint, wherein said slot includes an increasing radius.

4. The device of claim 1, wherein said pivotal connection between said first hinge portion and said second hinge portion further comprises:

two pins;

two apertures formed through an area of one of said first and second hinge portions; and first and second elongated slots formed through an area of the other of said first and second hinge portions, the first slot defining a longitudinal axis having a direction corresponding to a distraction of the joint, and the second slot defining a curved shape corresponding to a movement of the joint resulting in a distraction of the joint;

whereby one each of said two pins pass through said first and second slots, respectively, connecting said first and second hinge portions, whereby said first and second hinge portions are constrained relative to each other to define an arc of movement corresponding to a distraction of the joint as an angle of said second hinge is increased.

5. The device of claim 1, wherein said drive assembly further comprises a ratchet and a pawl.

6. The device of claim 1, wherein said rotation control subassembly comprises a projection associated with said second raceway operative to block movement of said rotatable element to said position in binding conformity.

7. The device of claim 1, wherein said drive assembly further comprises a clutch configured to prevent rotation of said spool in a direction to release a tension of said cable.

8. A device for stretching tissue of a joint in a body of a patient, comprising:

a first hinge including a first hinge portion affixable to a first portion of the patient's body on a first side of the joint; and a second hinge portion pivotally connected to said first hinge portion, affixable to a second portion of the patient's body on a second side of the joint;

a spool associated with said first hinge portion;

a first pulley associated with said second hinge portion;

a cable extending between said spool and said first pulley;

a drive shaft configured to apply a rotational force to said first pulley whereby a tension is applied to said cable and said first hinge portion is urged to move relative to said second hinge portion;

a drive assembly configured to limit a rotation of said first pulley, said drive assembly including a first circular raceway;

at least one rotatable element; and a second raceway disposed in concentrically rotating conformity with said first circular raceway, having at least one curved surface operative to support said rotatable element between said first and second raceways, whereby when said first circular raceway is rotated in a first direction, said curved surface urges said rotatable element to a position in binding conformity between said first and second raceways, preventing rotation of said first raceway with respect to said second raceway; and a plurality of pins configured to prevent said rotatable element from moving to said position in binding conformity when said second raceway is rotated.

9. The device of claim 8, wherein said second raceway comprises a projection operative to block movement of said rotatable element to said position in binding conformity.

10. The device of claim 8, further including:

a second pulley associated with said first and second hinge portions;

whereby said cable passes through said first and second pulleys.

11. The device of claim 8, wherein said drive assembly is configured to limit a rotation in both directions of rotation of said first pulley.

12. The device of claim 8, wherein said cable is resilient.

13. A device for stretching tissue of a joint in a body of a patient, comprising:

a first hinge including a first hinge portion affixable to a first portion of the patient's body on a first side of the joint; and a second hinge portion pivotally connected to said first hinge portion, affixable to a second portion of the patient's body on a second side of the joint;

a second hinge connected between said first and second hinge portions;

a cable extending between one of said first and second hinge portions and said second hinge;

a spool, connected to said cable, operative to apply a tension to said cable to increase an angle of said second hinge, thereby increasing an angle of said first hinge to cause stretching of joint tissue;

a drive assembly configured to limit a rotation of said spool, including a first circular raceway connected to said spool;

at least one rotatable element; and a second raceway disposed in concentrically rotating conformity with said first circular raceway, having at least one curved surface operative to support said rotatable element between said first and second raceways, whereby when said first circular raceway is rotated in a first direction, said curved surface urges said rotatable element to a position in binding conformity between said first and second raceways, preventing rotation of said first raceway with respect to said second raceway; and a plurality of pins configured to prevent said rotatable element from moving to said position in binding conformity when said second raceway is rotated.

14. The device of claim 13, wherein said cable is resilient, and wherein said resilience of said cable is operative to impart a continuous force to said first and second hinges in a direction of increasing an angle of said first and second hinges.

* * * * *